(12) United States Patent
Sugiura et al.

(10) Patent No.: US 10,723,625 B2
(45) Date of Patent: Jul. 28, 2020

(54) METHOD FOR PRODUCING OCTACALCIUM PHOSPHATE SHAPED PRODUCT

(71) Applicant: GC Corporation, Shizuoka (JP)

(72) Inventors: Yuki Sugiura, Fukuoka (JP); Kunio Ishikawa, Fukuoka (JP)

(73) Assignee: GC CORPORATION, Shizuoka (JP)

( * ) Notice: Subject to any disclaimer, the term of this patent is extended or adjusted under 35 U.S.C. 154(b) by 0 days.

(21) Appl. No.: 16/621,882

(22) PCT Filed: Jun. 15, 2018

(86) PCT No.: PCT/JP2018/022823
§ 371 (c)(1),
(2) Date: Dec. 12, 2019

(87) PCT Pub. No.: WO2018/230675
PCT Pub. Date: Dec. 20, 2018

(65) Prior Publication Data
US 2020/0115231 A1  Apr. 16, 2020

(30) Foreign Application Priority Data
Jun. 16, 2017 (JP) ................................ 2017-118406

(51) Int. Cl.
| | | |
|---|---|---|
| C01B 25/32 | (2006.01) | |
| B01J 20/04 | (2006.01) | |
| B01J 20/30 | (2006.01) | |
| B01J 20/28 | (2006.01) | |
| B01J 27/18 | (2006.01) | |
| B01J 35/10 | (2006.01) | |
| B01J 37/03 | (2006.01) | |
| B01J 37/04 | (2006.01) | |

(52) U.S. Cl.
CPC .......... *C01B 25/322* (2013.01); *B01J 20/048* (2013.01); *B01J 20/28085* (2013.01); *B01J 20/3085* (2013.01); *B01J 27/1806* (2013.01); *B01J 35/1076* (2013.01); *B01J 37/031* (2013.01); *B01J 37/04* (2013.01); *C01P 2002/72* (2013.01); *C01P 2002/82* (2013.01); *C01P 2004/02* (2013.01); *C01P 2004/03* (2013.01); *C01P 2006/16* (2013.01)

(58) Field of Classification Search
None
See application file for complete search history.

(56) References Cited

U.S. PATENT DOCUMENTS

| | | |
|---|---|---|
| 2010/0055018 A1 | 3/2010 | Bohner |
| 2017/0209626 A1 | 7/2017 | Deev et al. |

FOREIGN PATENT DOCUMENTS

| | | |
|---|---|---|
| EP | 3130342 | 2/2017 |
| JP | 5-70113 | 3/1993 |
| JP | 8-261474 | 10/1996 |
| JP | 2001-333974 | 12/2001 |
| JP | 2005-67966 | 3/2005 |
| JP | 2010-523232 | 7/2010 |

OTHER PUBLICATIONS

O. Suzuki et al., "Adsorption of Bovine Serum Albumin onto Octacalcium Phosphate and its Hydrolyzates", Cells and Materials, vol. 5, No. 1, 1995, pp. 45-54.
S. Kamakura et al., "Implanted octacalcium phosphate is more resorbable than ß-tricalcium phosphate and hydroxyapatite", J Biomed Mater Res 59, 2002, pp. 29-34.
Racquel Z. LeGeros, "Preparation of Octacalcium Phosphate (OCP): A Direct Fast Method", Calcified Tissue International 37, 1985, pp. 194-197.
Masanobu Kamitakahara et al., "Synthesis of Calcium Phosphates Containing Metal Ions and Evaluation of their Catalytic Activity for the Decomposition of Hydrogen Peroxide", Journal of the Ceramic Society of Japan 115 [7], 2007, pp. 425-428.
S. Kamakura et al., "Implantation of Octacalcium Phosphate (OCP) in Rat Skull Defects Enhances Bone Repair", J Dent Res 78(11), Nov. 1999, pp. 1682-1687.
O. Suzuki, "Octacalcium phosphate: Osteoconductivity and crystal chemistry", Acta Biomaterialia 6, Apr. 4, 2010, pp. 3379-3387.
ISR in International Patent Application No. PCT/JP2018/022823, dated Sep. 18, 2018, English translation.
IPRP International Patent Application No. PCT/JP2018/022823, dated Dec. 17, 2019, English translation.

*Primary Examiner* — Nannette Holloman
(74) *Attorney, Agent, or Firm* — Greenblum & Bernstein, P.L.C.

(57) ABSTRACT

The present invention provides: a method for producing a shaped product comprising octacalcium phosphate and having a volume of 2.0 mm$^3$ or more, comprising immersing a precursor ceramic composition containing at least one of Ca and PO$_4$ in composition, having a solubility in H$_2$O higher than that of octacalcium phosphate, and having a volume greater than 2.0 mm$^3$, in a solution containing a component which is not contained in the precursor ceramic composition, among the components Ca, PO$_4$ and H$_2$O, which are components of octacalcium phosphate to allow the precursor ceramic composition to react, thereby converting at least a part of the precursor ceramic composition into octacalcium phosphate; and the like.

19 Claims, 14 Drawing Sheets

[Figure 1-1]
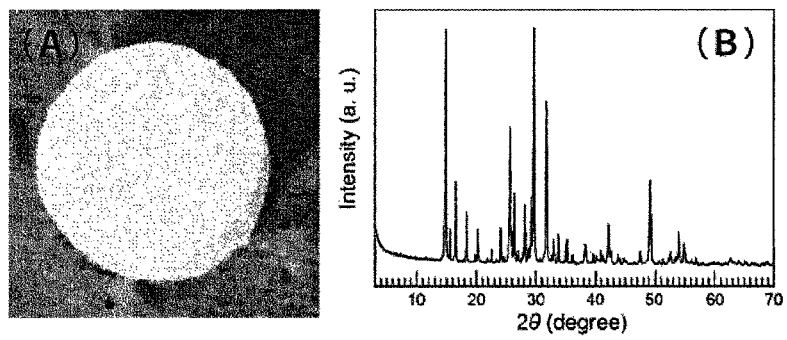
[Figure 1-2]
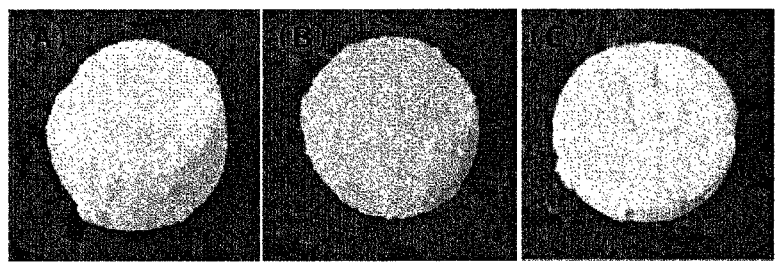
[Figure 1-3]
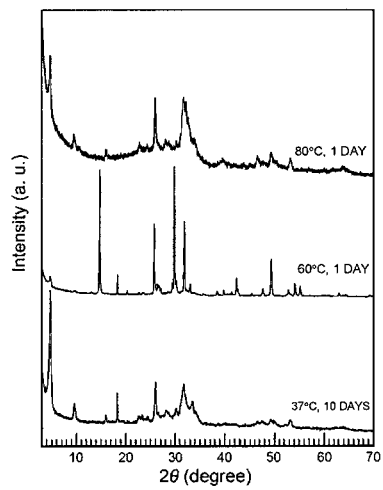

[Figure 1-4]
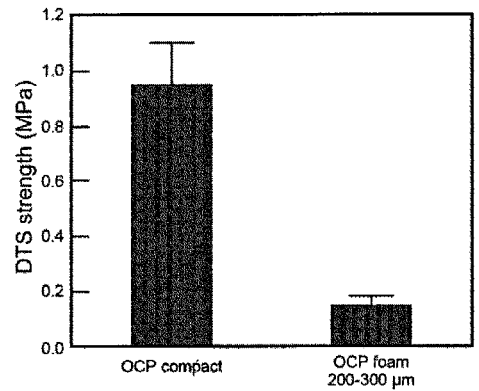
[Figure 1-5]
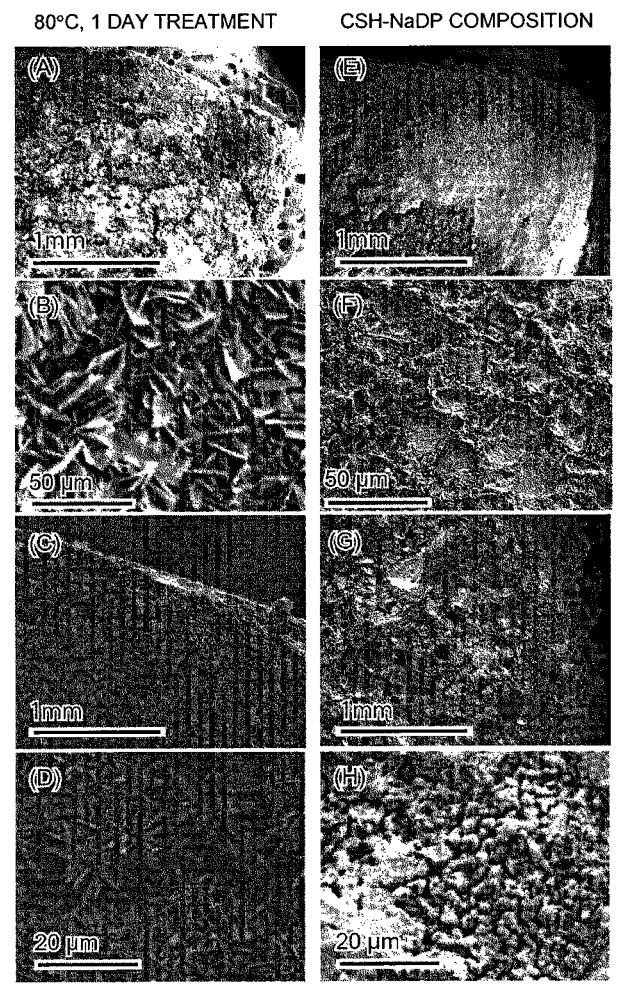

[Figure 2-1]
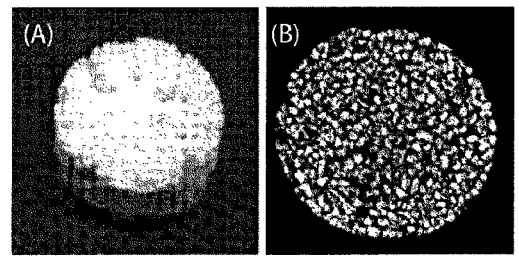
[Figure 2-2]
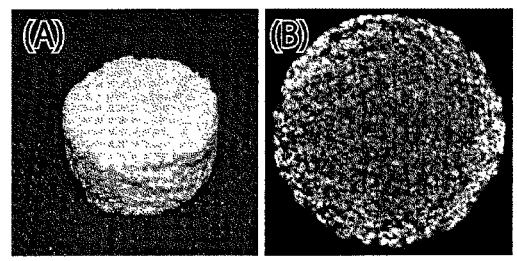
[Figure 2-3]
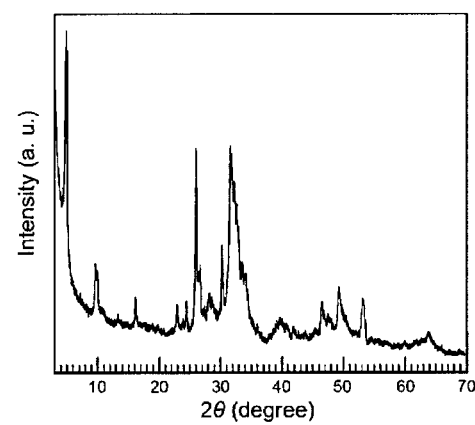

[Figure 2-4]
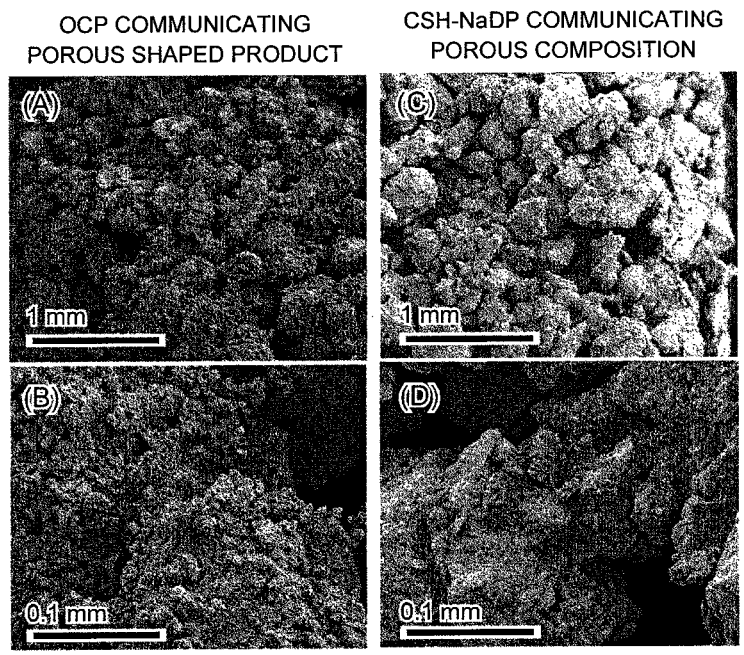
[Figure 2-5]
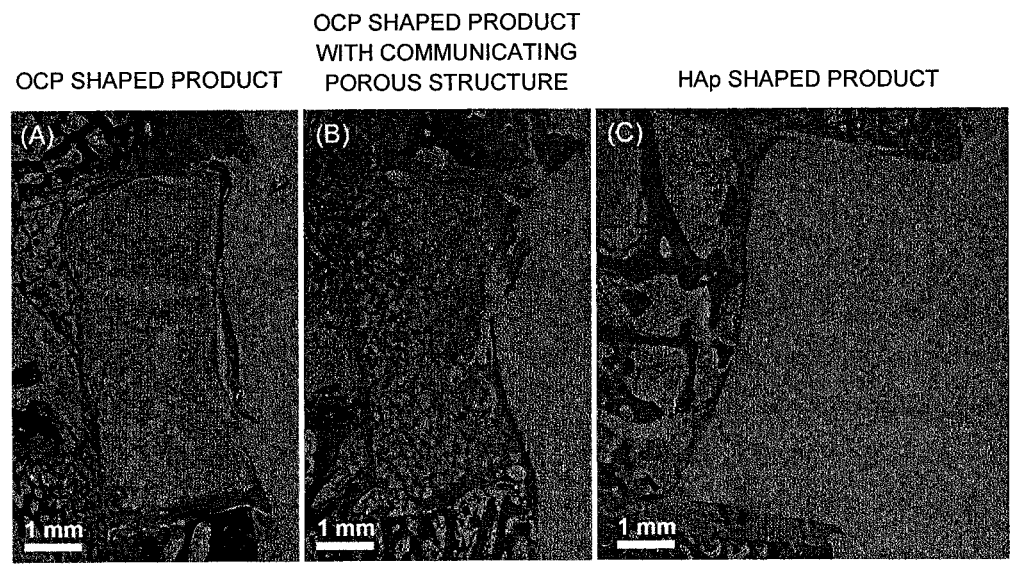

[Figure 2-6]
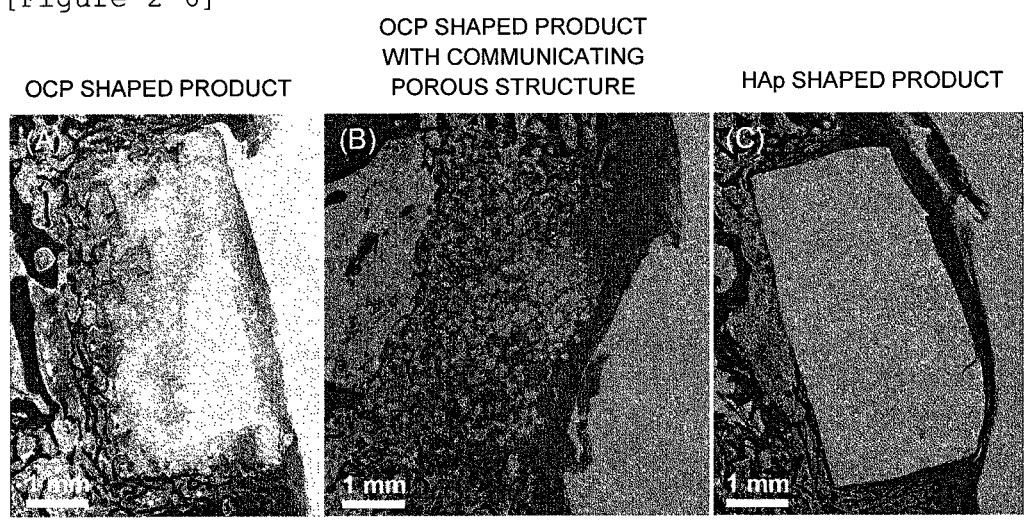
OCP SHAPED PRODUCT
OCP SHAPED PRODUCT WITH COMMUNICATING POROUS STRUCTURE
HAp SHAPED PRODUCT
[Figure 3-1]
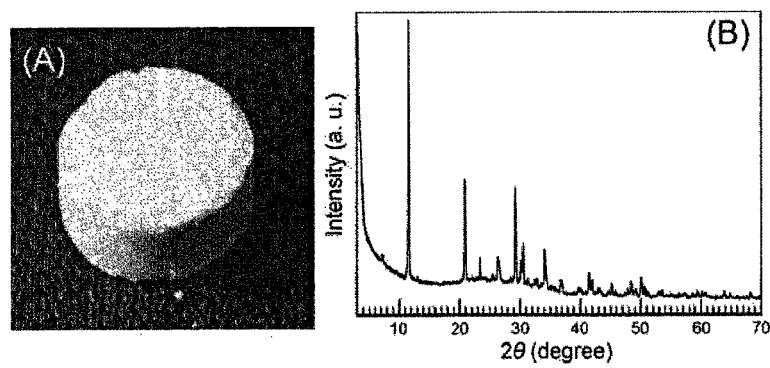

[Figure 3-2]
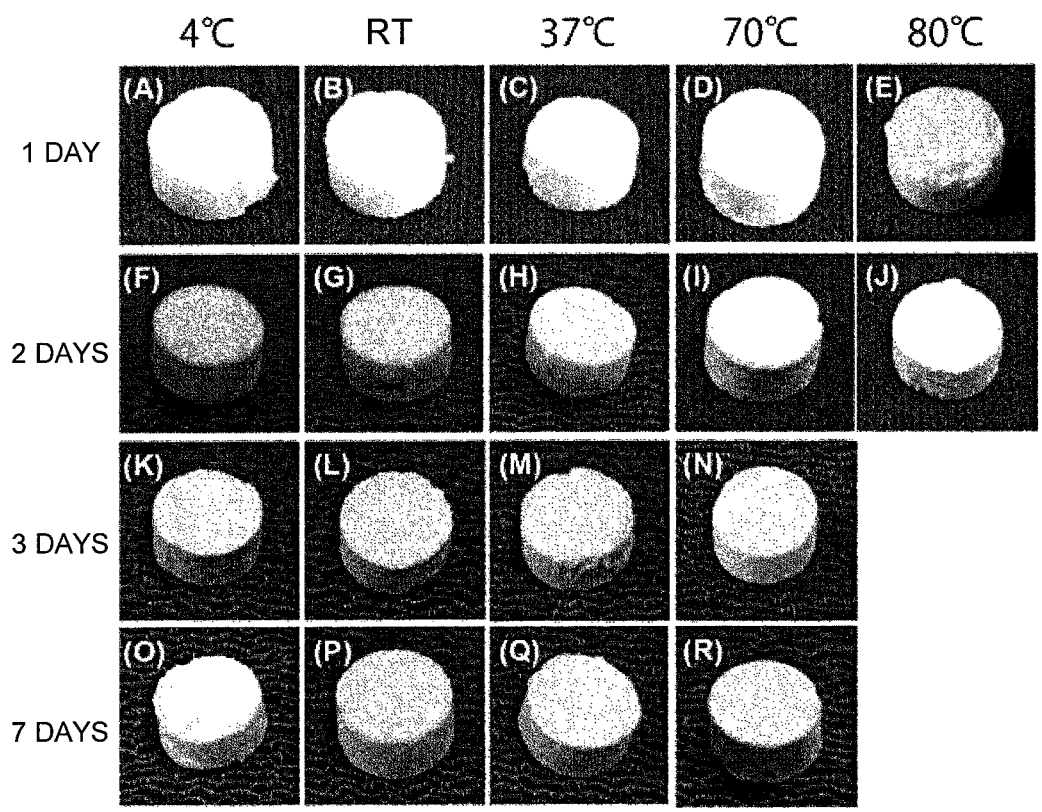

[Figure 3-3]
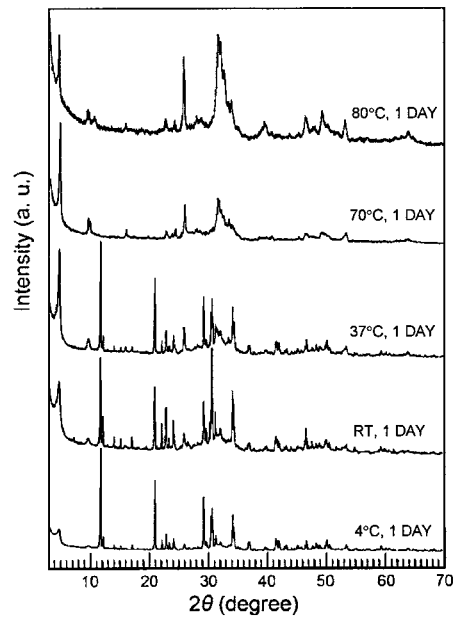
[Figure 3-4]
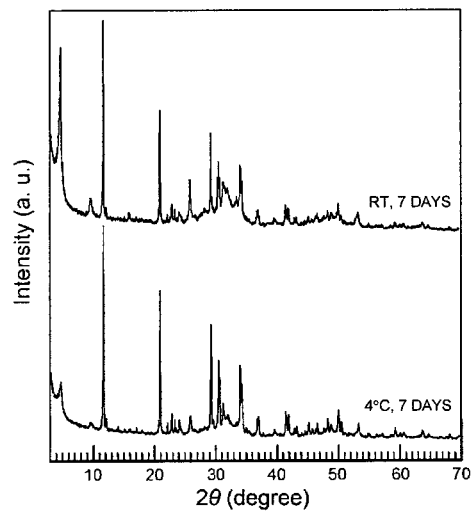

[Figure 3-5]
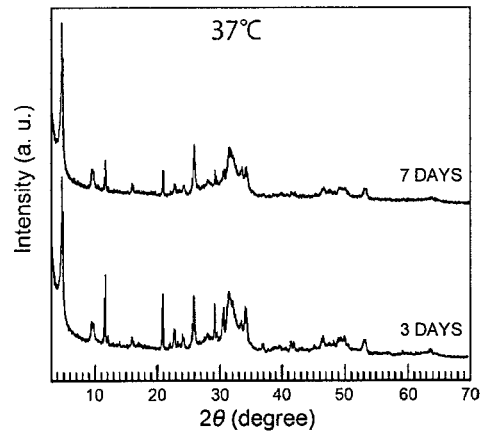
[Figure 3-6]
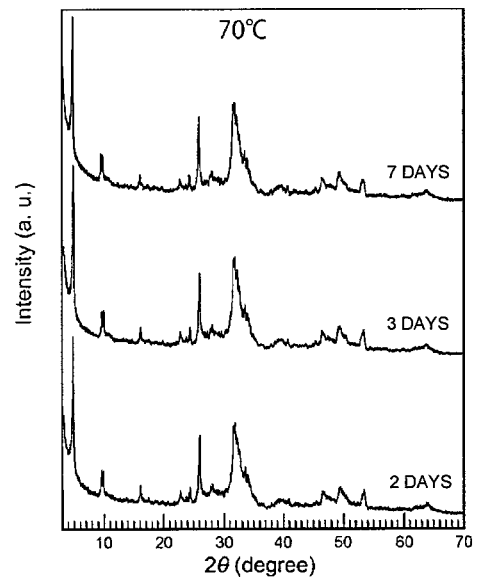

[Figure 3-7]
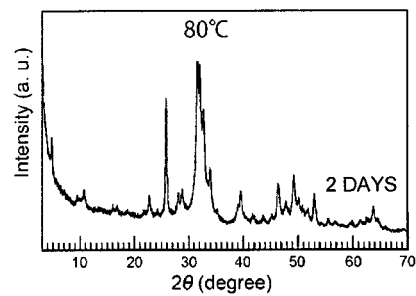
[Figure 3-8]
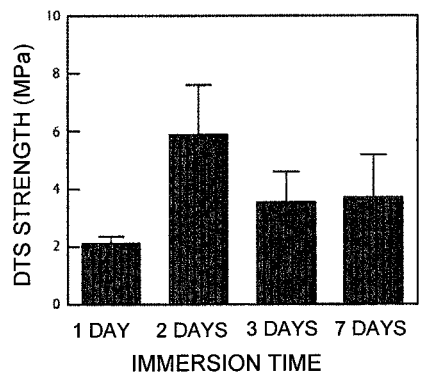
[Figure 4-1]
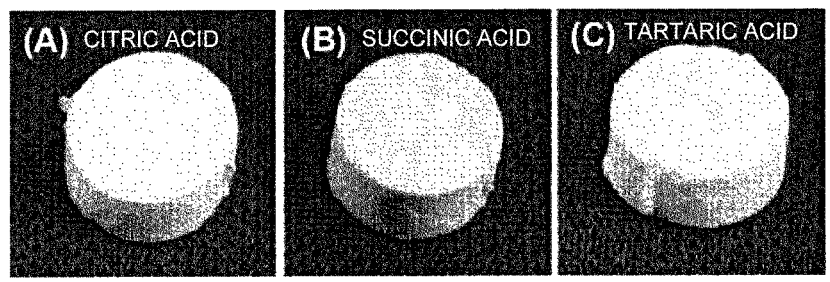

[Figure 4-2]
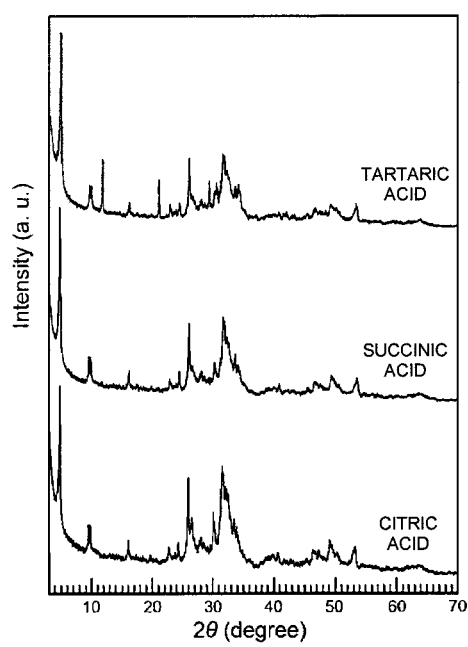

[Figure 4-3]
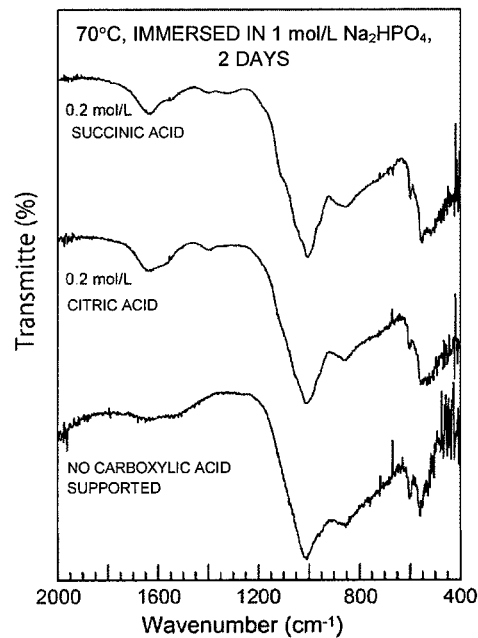
[Figure 4-4]
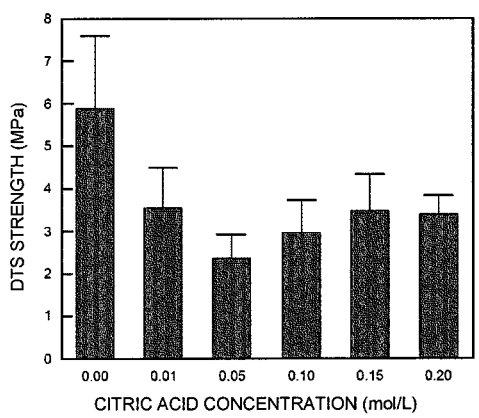

[Figure 4-5]
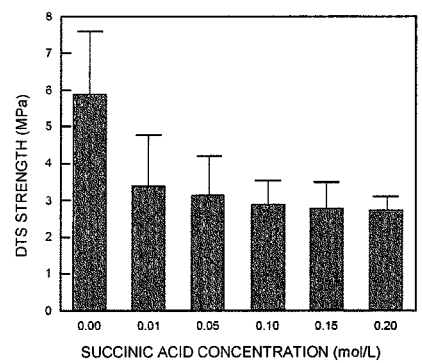
[Figure 5-1]
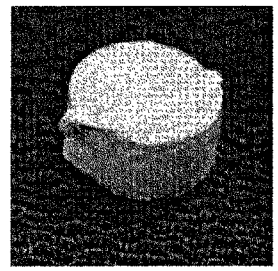
[Figure 5-2]
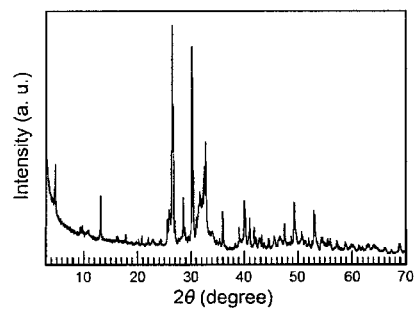

[Figure 5-3]
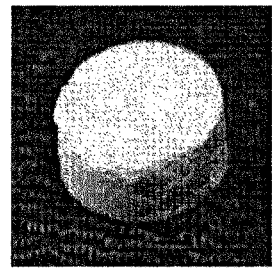
[Figure 5-4]
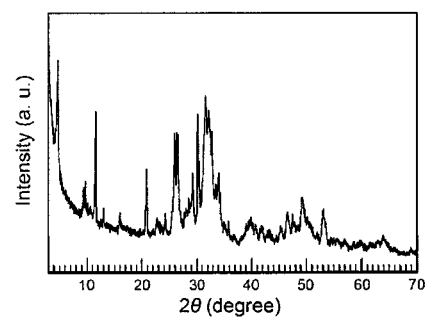
[Figure 6-1]
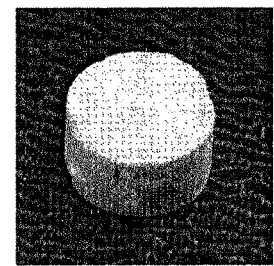

[Figure 6-2]
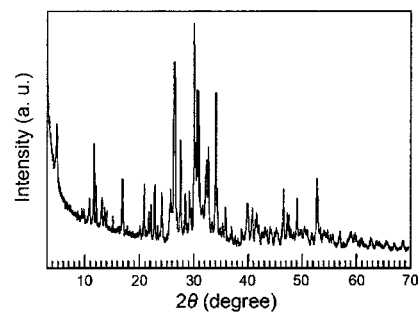
[Figure 7-1]
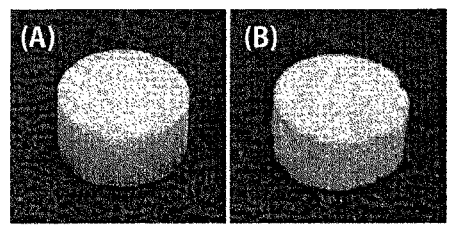
[Figure 7-2]
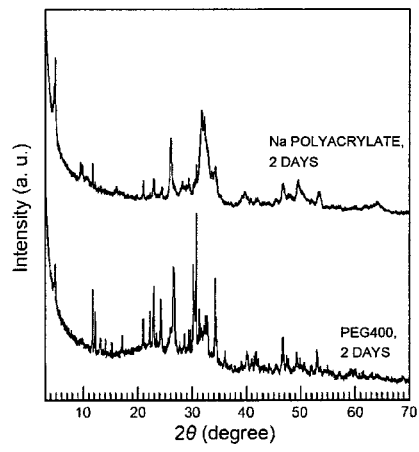

METHOD FOR PRODUCING OCTACALCIUM PHOSPHATE SHAPED PRODUCT

TECHNICAL FIELD

The present invention relates to a method for producing an octacalcium phosphate shaped product that can be used for bone regeneration materials, harmful molecule adsorbing materials, catalyst supporting materials, chemical agent supporting materials and the like.

BACKGROUND ART

Octacalcium phosphate (OCP) is a metastable phase of calcium phosphate preferentially crystallized from a solution thereof under a pH condition of 4 to 7, and is a precursor of an apatite. From the research so far, it has been known that this OCP is useful as a bone regeneration material, an organic molecule adsorbing material, and a catalyst supporting material (see Non Patent Literatures 1 to 3). Further, it is expected that, by imparting a porous structure to this material, bone regeneration reaction, organic molecule adsorption reaction and catalytic effect, all of which are reactions occurring via the surface of the material, are promoted.

OCP is not sinterable, and it is impossible to produce a shaped product with a complicated shape utilizing a curing process of the shaped product over the course of sintering. The known methods such as the drop method by LeGeros and the method using a three-way pipe by Suzuki et al. can produce OCP powder or granule, but the maximum size of OCP that can be formed is not more than $1.0 \text{ mm}^3$ (see Patent Literature 1, and Non Patent Literatures 4 and 5).

This conventional OCP shaped product is produced via crystal growing process, and therefore, the granule size is the largest size it can be. When it is used as a bone regeneration material, it is necessary to embed a large number of granules to the bone defect part (see Non Patent Literature 6). Further, the size and shape of voids between granules formed at this moment is not necessarily the optimal shape for the application. Furthermore, there is also a risk that granules flow out due to factors such as blood flow and air flow.

In order to solve such problems, there is a need to make the size of the shaped product $2.0 \text{ mm}^3$ or more.

CITATION LIST

Patent Literatures

Patent Literature 1: Japanese Patent Laid-Open Publication No. 5-70113

Non Patent Literatures

Non Patent Literature 1: J Biomed Mater Res 59: 29-34, 2002
Non Patent Literature 2: J Ceram Soc Jpn 115: 425-428, 2007
Non Patent Literature 3: Cell Mater 5: 45-54, 1995
Non Patent Literature 4: Calcif Tissue Int 37: 194-197, 1983
Non Patent Literature 5: Acta Biomater 6: 3379-3387, 2010
Non Patent Literature 6: J Dent Res 78: 1682-1687, 1999

SUMMARY OF INVENTION

Technical Problem

An object of the present invention is to provide a large sized OCP shaped product that can be applied to bone regeneration materials, harmful molecule adsorbing materials, catalyst supporting materials, chemical agent supporting materials and the like, and a method for producing the same.

Solution to Problem

The present inventors have so far shown that, by using a ceramic shaped product having a solubility higher than that of carbonic acid-containing apatite and containing at least one out Ca, $PO_4$ and $CO_3$ as a precursor, such as calcium sulfate dihydrate (CSD), and by immersing it in a solution containing all ions not contained in the ceramic among Ca, $PO_4$ and $CO_3$, a liquid phase mediated-dissolution precipitation reaction occurs and a carbonic acid-containing apatite, which is the most thermodynamically stable phase, is formed. It is known that a carbonic acid-containing apatite (carbonate apatite, $CO_3Ap$) shaped product that is formed via the liquid phase mediated-dissolution precipitation reaction mostly maintains the shape of the ceramic shaped product, which is the precursor.

However, OCP is not the most thermodynamically stable phase, and it is compositionally converted into an apatite or the like through contact with a liquid phase.

The present inventors have found that, OCP, which is not the thermodynamically most stable phase, can also be produced under specific conditions through composition conversion reaction, thereby completing the present invention. In other words, the present inventors have found that even a metastable phase can be formed via a composition conversion reaction as long as OCP has a solubility smaller than that of the ceramic immersed in the solution. Further, if the structure of the shaped product is chemically retained due to entanglement between crystals of the metastable phase or the like, a shaped product composed of the metastable phase can be obtained. In this case, a stable phase is formed later than the metastable phase, and therefore, the reaction needs to be terminated before the stable phase is formed, and replacing the metastable phase.

The stable phase herein refers to a phase that is formed when the reaction is allowed to continue for a sufficient time under certain temperature, pressure, chemical composition and pH conditions, and that is not further compositionally converted into another phase. It is a phase with the thermodynamically lowest energy level. When only the stable phase is present, naturally no further reaction occurs, and if the reaction is carried out in a solution, change in the pH of the solution does not occur.

Specifically, the present inventors have proceeded with various investigations, and as a result, have successfully produced a shaped product maintaining a general form of a precursor ceramic composition, cured by a chemical bond of an inorganic component, or entanglement or fusion between crystals of an inorganic component, having a volume of $2.0 \text{ mm}^3$ or more, and containing 10% by mass or more of OCP, by immersing a precursor ceramic composition containing at least one of Ca and $PO_4$, having a solubility in $H_2O$ higher than that of OCP (0.090 g/L), and having a volume greater than $2.0 \text{ mm}^3$, into a solution containing all of Ca, $PO_4$ or $H_2O$ which are not contained in composition of the precursor ceramic composition, and terminating the reaction before the reaction completion point, thereby completing the present invention.

Specifically, the present invention is as follows.

[1] A method for producing a shaped product comprising octacalcium phosphate and having a volume of 2.0 mm$^3$ or more, comprising immersing a precursor ceramic composition containing at least one of Ca and $PO_4$ in composition, having a solubility in $H_2O$ higher than that of octacalcium phosphate, and having a volume greater than 2.0 mm$^3$, in a solution containing a component which is not contained in the precursor ceramic composition, among the components Ca, $PO_4$ and $H_2O$, which are components of octacalcium phosphate to allow the precursor ceramic composition to react, thereby converting at least a part of the precursor ceramic composition into octacalcium phosphate.

[2] The method for producing a shaped product according to [1], wherein the precursor ceramic composition is converted into the shaped product comprising octacalcium phosphate by keeping a general form thereof.

[3] The method for producing a shaped product according to [1] or [2], wherein the shaped product comprising octacalcium phosphate is a shaped product containing 10% by mass or more of octacalcium phosphate.

[4] The method for producing a shaped product according to any one of [1] to [3], comprising removing the shaped product from the solution before a reaction completion point at which the precursor ceramic composition is compositionally converted into a substance in stabilized phase.

[5] The method for producing a shaped product according to [4], wherein the solution at the reaction completion point has a pH of 4 or more, and the reaction is terminated at a pH condition higher than the pH at the reaction completion point.

[6] The method for producing a shaped product according to [5], wherein a calcium phosphate component at the reaction completion point is an apatite.

[7] The method for producing a shaped product according to any one of [4] to [6], wherein the reaction is terminated at a point at which a $Ca/PO_4$ ratio of the shaped product is lower than a $Ca/PO_4$ ratio of the shaped product at the reaction completion point.

[8] The method for producing a shaped product according to any one of [4] to [7], wherein the reaction is terminated at a point at which a $Ca/PO_4$ ratio of the solution is higher than a $Ca/PO_4$ ratio of the solution at the reaction completion point.

[9] The method for producing a shaped product according to [4], wherein a pH at the reaction completion point is less than 4, and the reaction is terminated at a pH condition lower than the pH at the reaction completion point.

[10] The method for producing a shaped product according to [9], wherein a calcium phosphate component at the reaction completion point is dicalcium phosphate anhydrous or dicalcium phosphate dihydrate.

[11] The method for producing a shaped product according to [4], [9] or [10], wherein the reaction is terminated at a point at which a $Ca/PO_4$ ratio of the shaped product is higher than a $Ca/PO_4$ ratio of the shaped product at the reaction completion point.

[12] The method for producing a shaped product according to [4], [9], [10] or [11], wherein the reaction is terminated at a point at which a $Ca/PO_4$ ratio of the solution is lower than a $Ca/PO_4$ ratio of the solution at the reaction completion point.

[13] The method for producing a shaped product according to any one of [1] to [12], comprising allowing a substance including a functional group that chemically bonds to calcium in composition to be contained in at least one of the precursor ceramic composition and the solution, so that the substance including a functional group that chemically bonds to calcium in composition is supported on an octacalcium phosphate crystal.

[14] The method for producing a shaped product according to [13], wherein another substance is supported on the octacalcium phosphate crystal.

[15] A shaped product cured by a chemical bond of an inorganic component, or entanglement or fusion between crystals of an inorganic component, wherein the shaped product contains 10% by mass or more of octacalcium phosphate and has a volume of 2.0 mm$^3$ or more.

[16] The shaped product according to [15], wherein 97.5% by mass or more of the shaped product is composed of inorganic components.

[17] The shaped product according to [15] or [16], wherein the shaped product has a porous structure having an arbitrary shape with a pore size in the range of 0 to 2000 μm inside thereof, and has a porosity of 0 to 99%.

[18] The shaped product according to any one of [15] to [17], wherein a substance having a functional group that chemically bonds to calcium in composition is supported on an octacalcium phosphate crystal.

[19] The shaped product according to [18], wherein another substance is supported on the octacalcium phosphate crystal.

Advantageous Effects of Invention

According to the producing method of the present invention, a large sized OCP shaped product that can be suitably used for bone regeneration materials, harmful molecule adsorbing materials, catalyst supporting materials, chemical agent supporting materials and the like can be produced.

BRIEF DESCRIPTION OF DRAWINGS

FIG. 1-1 (A) is a photograph of calcium sulfate hemihydrate (CSH)-sodium dihydrogen phosphate dihydrate (NaDP) composition, which is a precursor ceramic composition produced in Example 1, and FIG. 1-1 (B) is the XRD pattern thereof.

FIG. 1-2 shows photographs of shaped products produced in Example 1, and (A) is of the one after immersion at 37° C. for 10 days, (B) of the one after immersion at 60° C. for 1 day, and (C) of the one after immersion at 80° C. for 1 day.

FIG. 1-3 shows XRD patterns of the shaped products produced in Example 1.

FIG. 1-4 shows the diametral tensile strength (DTS) of the shaped product (80° C., 1 day) produced in Example 1.

FIGS. 1-5 (A) to (D) are SEM photographs of the shaped product (80° C., 1 day) produced in Example 1, and (A) and (B) show the surface thereof, and (C) and (D) show the cross section thereof. FIGS. 1-5 (E) to (H) are SEM photographs of the CSH-NaDP composition, which is the precursor ceramic composition, and (E) and (F) show the surface thereof, and (G) and (H) show the cross section thereof.

FIG. 2-1 (A) is a photograph of a CSH-NaDP composition with a communicating porous structure, which is a precursor ceramic composition produced in Example 2, and FIG. 2-1 (B) is a micro CT image thereof.

FIG. 2-2 (A) is a photograph of a shaped product (80° C., 1 day) produced in Example 2, and FIG. 2-2 (B) is a micro CT image thereof.

FIG. 2-3 is the XRD pattern of the shaped product (80° C., 1 day) produced in Example 2.

FIGS. 2-4 (A) and (B) are SEM photographs of the OCP shaped product with a communicating porous structure produced in Example 2, and FIGS. 2-4 (C) and (D) are SEM photographs of the CSH-NaDP composition with a communicating porous structure, which is the precursor ceramic composition.

FIG. 2-5 shows HE stained tissue images taken 2 weeks after embedding in a rabbit femur head, and (A) shows the OCP shaped product produced in Example 1, (B) shows the OCP shaped product with a communicating porous structure produced in Example 2, and (C) shows a hydroxyapatite sintered body, which is a control.

FIG. 2-6 shows HE stained tissue images taken 4 weeks after embedding in a rabbit femur head, and (A) shows the OCP shaped product produced in Example 1, (B) shows the OCP shaped product with a communicating porous structure produced in Example 2, and (C) shows a hydroxyapatite (HAp) sintered body, which is a control.

FIG. 3-1 (A) is a photograph of a dicalcium phosphate dihydrate (DCPD) composition produced in Example 3, and FIG. 3-1 (B) is the XRD pattern thereof.

FIG. 3-2 shows photographs of OCP shaped products produced in Example 3, and (A) to (E) show those after immersion at 4° C. to 80° C. for 1 day, (F) to (J) show those after immersion at 4° C. to 80° C. for 2 days, (K) to (N) show those after immersion at 4° C. to 80° C. for 3 days, and (O) to (R) show those after immersion at 4° C. to 80° C. for 7 days.

FIG. 3-3 shows XRD patterns of OCP shaped products (at 4° C. to 80° C. for 1 day) produced in Example 3.

FIG. 3-4 shows XRD patterns of OCP shaped products (at 4° C. or room temperature for 7 days) produced in Example 3.

FIG. 3-5 shows XRD patterns of OCP shaped products (at 37° C. for 3 days or 7 days) produced in Example 3.

FIG. 3-6 shows XRD patterns of OCP shaped products (at 70° C. for 2 days, 3 days or 7 days) produced in Example 3.

FIG. 3-7 shows XRD patterns of OCP shaped products (at 80° C. for 2 days) produced in Example 3.

FIG. 3-8 shows DTS strengths of OCP shaped products (at 70° C. for 1 day to 7 days) produced in Example 3.

FIG. 4-1 shows photographs of OCP shaped products produced in Example 4, and (A) shows the one immersed in an aqueous solution of disodium hydrogen phosphate containing citric acid, (B) shows the one immersed in an aqueous solution of disodium hydrogen phosphate containing succinic acid, and (C) shows the one immersed in an aqueous solution of disodium hydrogen phosphate containing tartaric acid.

FIG. 4-2 shows XRD patterns of OCP shaped products produced in Example 4.

FIG. 4-3 shows FT-IR spectra of OCP shaped products (citric acid, succinic acid) produced in Example 4.

FIG. 4-4 shows DTS strengths of shaped products containing citric acid produced in Example 4(7).

FIG. 4-5 shows DTS strengths of shaped products containing succinic acid produced in Example 4(7).

FIG. 5-1 is a photograph of an OCP shaped product produced in Example 5.

FIG. 5-2 shows XRD patterns of OCP shaped products produced in Example 5.

FIG. 5-3 is a photograph of an OCP shaped product produced in Example 5.

FIG. 5-4 shows XRD patterns of OCP shaped products produced in Example 5.

FIG. 6-1 is a photograph of an OCP shaped product produced in Example 6.

FIG. 6-2 shows XRD patterns of OCP shaped products produced in Example 6.

FIG. 7-1 shows photographs of OCP shaped products produced in Example 7, and (A) shows an OCP shaped product immersed in poly(ethylene glycol) and (B) shows an OCP shaped product immersed in sodium polyacrylate.

FIG. 7-2 shows XRD patterns of OCP shaped products produced in Example 7.

DESCRIPTION OF EMBODIMENTS

The method for producing a shaped product comprising octacalcium phosphate (hereinafter, may be simply referred to as a shaped product) and having a volume of 2.0 mm³ or more of the present invention is characterized by comprising immersing a precursor ceramic composition containing at least one of Ca and $PO_4$ in composition, having a solubility in $H_2O$ higher than that of octacalcium phosphate, and having a volume greater than 2.0 mm³, in a solution containing a component which is not contained in the precursor ceramic composition, among the components Ca, $PO_4$ and $H_2O$, which are components of octacalcium phosphate to allow the precursor ceramic composition to react, thereby converting at least a part of the precursor ceramic composition into octacalcium phosphate.

<Precursor Ceramic Composition>

As described above, the precursor ceramic composition in the present invention contains at least one of Ca and $PO_4$ in composition, has a solubility in $H_2O$ higher than that of octacalcium phosphate, and has a volume greater than 2.0 mm³. Note that $PO_4$ is a general term for molecules or ions taking the form of $H_3PO_4$, $H_2PO_4^-$, $HPO_4^{2-}$ or $PO_4^{3-}$, and they may coexist depending on the condition of a solution, of course. Further, the concentration of $PO_4$ means the total of these molecules and ions.

A method for shaping this precursor ceramic composition is not particularly limited. For example, shaping may be carried out by utilizing a curing reaction of a precursor ceramic having self-hardenability, such as calcium sulfate, by a precipitation reaction of a salt through sintering and drying, or by a pressure shaping to form a powder compact.

The volume of the precursor ceramic composition is greater than 2.0 mm³ from the viewpoint of producing an OCP shaped product of 2.0 mm³ or more. The size of the precursor ceramic composition is practically taken over to the OCP shaped product, and therefore, the size may be adjusted appropriately depending on the purpose of producing. For example, it may be 5.0 mm³ or more, or 10.0 mm³ or more.

For the precursor ceramic composition in the present invention, for example, calcium sulfate hemihydrate (CSH), calcium sulfate dihydrate (CSD), calcium sulfate anhydrous (CSA), dicalcium phosphate dihydrate (DCPD), dicalcium phosphate anhydrous (DCPA), α-tricalcium phosphate (α-TCP), β-calcium phosphate (β-TCP), calcium carbonate, monocalcium phosphate monohydrate (MCPM), monocalcium phosphate anhydrous (MCPA), amorphous calcium phosphate (ACP), calcium hydroxide, and the like can be used. One of them may be used singly, or two or more of them may be used at the same time.

It suffices that the solubility in $H_2O$ of the precursor ceramic composition is higher than the solubility in $H_2O$ of OCP (0.090 g/L), and it is preferable that the former be twice as high as the latter, or even higher. A higher solubility can further promote the composition conversion of the precursor ceramic composition.

<Immersion Solution>

The solution herein refers to a liquid phase in which a solute component and a solvent component are dispersed stably, unifiedly, and uniformly in a macroscopic state. Microscopically, even when a colloidal particle, molecular cluster, solvated molecule, associated cluster or the like is present, if the liquid phase is flowable and uniform as a whole, it is encompassed in the solution.

Even when a substance not uniformly dispersed in the solution is present and the liquid phase macroscopically appears to be in the suspended state, this liquid phase may be regarded as a solution as long as the reaction of the present invention progresses. In other words, the solution herein is a general term for electrolytic solutions, nonelectrolytic solutions, electrolytic suspensions and nonelectrolytic suspensions. A solution in which water accounts for 50% by mass or more among liquids used as solvents is particularly referred to as an aqueous solution.

The immersion solution is not particularly limited as long as it contains all components among the components Ca, $PO_4$ and $H_2O$, which are components of OCP, not contained in the composition of the ceramic composition. For example, examples of the solution containing $PO_4$ include solutions of phosphoric acid, trisodium phosphate, disodium hydrogen phosphate, sodium dihydrogen phosphate, tripotassium phosphate, potassium dihydrogen phosphate, dipotassium hydrogen phosphate, triammonium phosphate, diammonium hydrogen phosphate and ammonium dihydrogen phosphate, and examples of the solution containing Ca include solutions of calcium chloride, calcium nitrate, calcium acetate, calcium lactate, calcium hydroxide and calcium bicarbonate.

When the precursor ceramic composition contains both Ca and $PO_4$ among the constituents of OCP and there is no need to obtain Ca and $PO_4$ from the solution, another solution may be used. In other words, distilled water, solutions of sodium carbonate, sodium bicarbonate, sodium sulfate, sodium bisulfate, sodium chloride, ammonium chloride, ammonium nitrate, sodium hydroxide, potassium hydroxide and the like can be used. Further, the ratio of $H_2O$ in solvents of the solution is not particularly limited.

When the precursor ceramic composition contains at least one of Ca and $PO_4$ among the constituents of OCP and further contain $H_2O$, and there is no need to obtain $H_2O$ from the solution, the OCP shaped product may be produced by immersing the precursor ceramic composition in a solvent containing a component not contained in the precursor ceramic composition out of Ca and $PO_4$, and not containing $H_2O$. Furthermore, when the precursor ceramic composition contains all components Ca, $PO_4$ and $H_2O$, which are the constituents of OCP, the OCP shaped product may be produced by immersing the precursor ceramic composition in a solution containing none of Ca, $PO_4$ and $H_2O$. Note that how the precursor ceramic composition contains $H_2O$ is not particularly limited. For example, examples thereof include crystalline water, gap water and attached water.

Examples of the solution for immersion include, other than water, monohydric alcohols including primary alcohols such as methanol, ethanol, propan-1-ol, butan-1-ol, pentan-1-ol, hexan-1-ol, heptan-1-ol, octan-1-ol, nonan-1-ol and decan-1-ol, secondary alcohols such as 2-propanol (isopropyl alcohol), butan-2-ol, pentan-2-ol, hexan-2-ol and cyclohexanol, tertiary alcohols such as tert-butyl alcohol, 2-methylbutan-2-ol, 2-methylpentan-2-ol, 2-methylhexan-2-ol, 3-methylpentan-3-ol and 3-methyloctan-3-ol; dihydric alcohols such as ethylene glycol and diethylene glycol; trihydric alcohols such as glycerin; aromatic ring alcohols such as phenol; polyethers such as poly(ethylene glycol) (PEG) and polypropylene glycol (PPG); polycarboxylic acids such as polyacrylic acid and polycarbamic acid; fatty acids such as acetic acid, valeric acid, caproic acid, lauric acid, palmitic acid, stearic acid, oleic acid and linoleic acid; alkanes such as pentane, butane, hexane, heptane and octane; ethers such as dimethyl ether, methyl ethyl ether and diethyl ether; aromatic compounds such as benzene, toluene, picric acid and TNT; polycyclic aromatic hydrocarbons such as naphthalene, azulene and anthracene; organic halogen compounds such as chloromethane, dichloromethane, chloroform and carbon tetrachloride; esters such as ethyl acetate, methyl butyrate, methyl salicylate, ethyl formate, ethyl butyrate, ethyl caproate, octyl acetate, dibutyl phthalate, ethylene carbonate and ethylene sulfide; cycloalkanes such as cyclopentane, cyclohexane and decalin; bicycloalkanes; ketones such as acetone, methyl ethyl ketone and diethyl ketone; aldehydes such as formaldehyde, acetaldehyde, propionaldehyde, butanal, pentanal, hexanal and vanillin; amine compounds such as aminomethane, aminoethane, ethylenediamine, triethylamine and aniline; saccharides such as glucose, fructose and threitol; thiols such as methanethiol, ethanethiol, propanethiol and thiophenol; and disulfide compounds such as dimethyl sulfide, diphenyl sulfide, asparagusic acid, cystamine and cystine. One of them may be used singly, or a plurality of them may be mixed for use.

<Reaction Conditions>

Immersion time of the precursor ceramic composition in the solution is adjusted such that OCP is formed and the reaction ends before the stable phase is formed. It is normally 10 minutes to 30 days, preferably 2 hours to 14 days, and further preferably 2 hours to 7 days.

When $PO_4$ and Ca ion are contained in the solution, the stable phase of calcium phosphate to be formed depends on the pH of the solution. Calcium phosphate herein refers to an inorganic compound that contains 50% by mass or more of Ca and $PO_4$ in composition, out of the components in the inorganic compound excluding water, and in which Ca has the largest ratio among cations in the composition thereof and $PO_4$ has the largest ratio among anions in composition.

When the pH of the solution is 4 or more, the stable phase is an apatite.

The apatite herein is a general term for substances categorized as calcium phosphate that have the following chemical composition and are the most thermodynamically stable phases in a solution with a pH of 4 or more compared to calcium phosphate that does not fall within the scope of this term. In other words, the apatite refers to a substance represented by $Ca_{10-x}Q_y(PO_4)_{6-z}R_wJ_v$, wherein Q is any of cations such as Na, Mg, Fe, K, Sr, Rb, Zn, Ga, Al, Mn, Cu, Mo, Ag, Au, Se and Te or a void; R is any of anions such as $HPO_4$, $SO_4$, $CO_3$, $BO_3$, $WO_4$, $VO_4$ and $SiO_4$ or a void; J is any of anions such as OH, Cl, F, Br and I; X<5, Y<5, Z<3, W<3; and the total of Ca and $PO_4$ is 50 atomic % or more.

Specifically, examples of the apatite include substances such as hydroxyapatite ($Ca_{10}(PO_4)_6(OH)_2$, HAp), calcium-deficient apatite ($Ca_9(HPO_4)_4(PO_4)_2(OH)$), fluorapatite ($Ca_{10}(PO_4)_6F_2$), chlorapatite ($Ca_{10}(PO_4)_6Cl_2$) and $CO_3Ap$. The Ca/$PO_4$ molar ratio of these substances is normally 1.50 to 2.50, and 1.67 in the case of stoichiometric HAp.

When the apatite is formed from the solution, it is known that it may be formed via a metastable phase. When the solution has a pH of 4 or more, a phase other than the stable phase, apatite, is compositionally converted into an apatite and disappears eventually when the apatite is formed.

OCP is a metastable phase of the apatite, and therefore, if it is immersed in the solution for a long period of time and the reaction is allowed to continue in a solution with a pH of 4 or more, it is eventually converted into the apatite. However, when an apatite is formed through a reaction path in which OCP is formed from the precursor, OCP can be obtained by terminating the reaction before the formation of the apatite.

In other words, a shaped product composed of OCP can be obtained by terminating the reaction after OCP is formed from a ceramic shaped product, which is the precursor and before the composition conversion of OCP to the apatite is completed.

In order to terminate the reaction, in case of a shaped product, an operation of separating the shaped product from the solution is necessary. In other words, the reaction can be terminated by carrying out an operation of removing the shaped product from the solution in which the shaped product has been immersed and removing the solution attached to the shaped product. In the present invention, a time point at which the shaped product is taken out the immersion solution is defined as the termination point of reaction.

The operation of clearing the solution attached to the shaped product is not particularly limited. Normally, the shaped product is washed multiple times with a solvent such as distilled water or ethanol, the solution attached to the shaped product is replaced by such a solvent, and an excessive solvent is cleaned with a filter paper and dried.

The chemical reaction formula when OCP is compositionally converted into HAp is as follows:

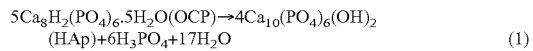

$$5Ca_8H_2(PO_4)_6 \cdot 5H_2O(OCP) \rightarrow 4Ca_{10}(PO_4)_6(OH)_2 (HAp) + 6H_3PO_4 + 17H_2O \quad (1)$$

Since $H_3PO_4$ formed in the reaction of formula (1) described above shows acidity, when the apatite is formed from OCP, the pH of the surrounding solution declines. In other words, when compared with the pH at a time point where OCP is formed and still present, the solution has a lower pH at a time point where the composition conversion into the apatite advances, thereby achieving a single phase of apatite. By utilizing this, pH can be used as an indicator for terminating the reaction before OCP is compositionally converted into the apatite.

In the reaction of formula (1) described above, the pH of the solution decreases, but how much it decreases depends on the mass ratio of the solution and the shaped product, and on the buffering action by ions contained in the solution. However, in any case, the pH no longer varies at a reaction completion point where OCP disappears, only leaving the apatite.

In the present specification, a time point where calcium phosphate is converted into a single phase of apatite in a powder X-ray diffraction analysis and the pH no longer varies is defined as a time point where no further reaction occurs, that is, the reaction completion point, and the pH at this time point is defined as the pH at the reaction completion point.

The pH at the reaction completion point is not particularly limited, but is preferably 4 or more, more preferably 4 to 10, and further preferably 4 to 7.

If the pH at the reaction completion point is 4 or more, the pH of the solution when terminating the reaction is not particularly limited as long as it is higher than that value. It is preferably higher than the pH at the reaction completion point by 0.1 or more, and further preferably t by 0.2 or more.

Further, the chemical composition of OCP is $Ca_8H_2(PO_4)_6 \cdot 5H_2O$, and therefore, the stoichiometric $Ca/PO_4$ ratio is 1.33. Accordingly, when the apatite is formed from OCP, from the viewpoint of stoichiometry, excessive $PO_4$ needs to be released into the surrounding solution, or deficient Ca needs to be absorbed from the surrounding solution.

In other words, when the apatite is formed from OCP, the $Ca/PO_4$ ratios of the solution and the shaped product vary. By utilizing this, the $Ca/PO_4$ ratios can be used as an indicator for terminating the reaction before OCP is compositionally converted into the apatite. Further, the variation of the $Ca/PO_4$ ratios of the solution and the shaped product at this time is dependent on the mass ratio of the shaped product and the solution, and the concentration of Ca or $PO_4$ contained in the solution. However, in any case, $Ca/PO_4$ of the shaped product and the solution no longer varies at the reaction completion point where OCP is compositionally converted into the apatite completely, only leaving the stable phase.

The $Ca/PO_4$ ratio of the shaped product at the reaction completion point is not particularly limited. If it is a single phase of apatite, the ratio is normally 1.5 to 2.0.

In case where the calcium phosphate of the shaped product at the reaction completion point is composed of the apatite, the $Ca/PO_4$ ratio of the shaped product upon terminating the reaction is not particularly limited as long as it is higher than the $Ca/PO_4$ ratio of the apatite.

In case where the calcium phosphate of the shaped product at the reaction completion point is composed of apatite, the $Ca/PO_4$ ratio of the solution upon terminating the reaction is not particularly limited as long as it is lower than the $Ca/PO_4$ ratio of the solution at that reaction completion point.

Here, as one embodiment in a system in which an apatite is the stable phase, it is preferable to produce the OCP shaped product by immersing an acidic precursor ceramic composition in a solution with a pH of 4 to 14, preferably in a solution with a pH of greater than 7 to 12 and retaining it until the pH becomes 4 to 7. In this embodiment, OCP is generated from the raw material, precursor ceramic composition via generation of ACP. ACP, production of which is promoted at a high pH region, is effectively produced in the solution with a high pH, and OCP, production of which is promoted at a low pH region, is effectively produced due to a low pH that the precursor ceramic composition itself has. Accordingly, it is believed that the composition conversion of the precursor to the OCP shaped product is carried out effectively.

On the other hand, in case where the solution has a pH of less than 4, the stable phase is DCPA or DCPD. $Ca/PO_4$ of DCPA and DCPD is theoretically 1.00. DCPD is a stable phase at less than 200° C., and DCPA is a stable phase at 200° C. or more (Ame. Mine. 2011, 96, 368-373, 2011).

In case where the solution has a pH of less than 4, a phase other than the stable phase, DCPD or DCPA, is compositionally converted into DCPD or DCPA and disappears eventually when DCPD or DCPA is formed.

OCP is a metastable phase of DCPD or DCPA, and therefore, if it is immersed in the solution for a long period of time and the reaction is allowed to continue in a solution with a pH of less than 4, it is eventually converted into DCPD or DCPA. However, when DCPD or DCPA is formed through a reaction path in which OCP is formed from the precursor, OCP can be obtained by terminating the reaction before the formation of DCPD or DCPA.

The chemical reaction formula when OCP is compositionally converted into DCPD is as follows:

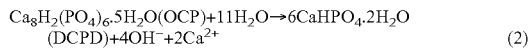
$$Ca_8H_2(PO_4)_6 \cdot 5H_2O(OCP) + 11H_2O \rightarrow 6CaHPO_4 \cdot 2H_2O (DCPD) + 4OH^- + 2Ca^{2+} \quad (2)$$

Further, the chemical reaction formula when OCP is compositionally converted into DCPA is as follows:

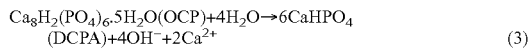
$$Ca_8H_2(PO_4)_6 \cdot 5H_2O(OCP) + 4H_2O \rightarrow 6CaHPO_4 (DCPA) + 4OH^- + 2Ca^{2+} \quad (3)$$

In the reactions of formulas (2) and (3) described above, when DCPD or DCPA is formed from OCP, the pH of the surrounding solution increases. In other words, when compared with the pH at a time point where OCP is formed and still present, the solution has a higher pH at a time point where the composition conversion into DCPD or DCPA advances, thereby becoming a single phase of DCPD or DCPA. By utilizing this, pH can be used as an indicator for terminating the reaction before OCP is compositionally converted into DCPD or DCPA.

In the reactions of formulas (2) and (3) described above, the pH of the solution increases, but how much it rises is dependent on the mass ratio of the solution and the shaped product, and on the buffering action by ions contained in the solution. However, in any case, the pH no longer varies at the reaction completion point where OCP disappears, only leaving DCPD and DCPA.

In the present specification, a time point where calcium phosphate becomes only into DCPD or DCPA in a powder X-ray diffraction analysis and the pH no longer varies is defined as a time point where no further reaction occurs, that is, the reaction completion point, and the pH at this time point is defined as the pH at the reaction completion point.

If the pH at the reaction completion point is less than 4, the pH of the solution when terminating the reaction is not particularly limited as long as it is lower than that value. It is preferably lower than the pH at the reaction completion point by 0.1 or more, and further preferably by 0.2 or more.

Further, the chemical composition of OCP is $Ca_8H_2(PO_4)_6 \cdot 5H_2O$, and therefore, the stoichiometric $Ca/PO_4$ ratio is 1.33. Accordingly, when DCPD is formed from OCP, from the viewpoint of stoichiometry, excessive Ca needs to be released into the surrounding solution, or insufficient $PO_4$ needs to be absorbed from the surrounding solution.

In other words, when DCPD and DCPA are formed from OCP, the $Ca/PO_4$ ratios of the solution and the shaped product vary. By utilizing this, the $Ca/PO_4$ ratios can be used as an indicator for terminating the reaction before OCP is compositionally converted into the apatite. Further, the variation of the $Ca/PO_4$ ratios of the solution and the shaped product at this time is dependent on the mass ratio of the shaped product and the solution, and on the concentration of Ca or $PO_4$ contained in the solution. However, in any case, $Ca/PO_4$ of the shaped product and the solution no longer varies at the reaction completion point where OCP is compositionally converted into DCPD and DCPA completely, only leaving the stable phase.

The $Ca/PO_4$ ratio of the shaped product at the reaction completion point is not particularly limited. In case it is a single phase of DCPD or DCPA, the ratio is normally 0.8 to 1.2.

In case where the calcium phosphate of the shaped product at the reaction completion point is composed of DCPD or DCPA, the $Ca/PO_4$ ratio of the shaped product when terminating the reaction is not particularly limited as long as it is lower than the $Ca/PO_4$ ratio of the shaped product at the reaction completion point.

If the calcium phosphate of the shaped product at the reaction completion point is composed of DCPD or DCPA, the $Ca/PO_4$ ratio of the solution when terminating the reaction is not particularly limited as long as it is higher than the $Ca/PO_4$ ratio of DCPD or DCPA.

Specifically, in the present invention, by preliminarily measuring how long it takes to obtain a stable phase under the same temperature and pressure conditions as the desired producing conditions by detecting change in the pH or variation of the $Ca/PO_4$ ratio during the reaction, the immersion time can be determined based on the preliminary time conditions.

The temperature at which the precursor ceramic composition is immersed in the solution is not particularly limited. It is normally −80° C. to 270° C., preferably 0° C. to 99° C., and more preferably 4° C. to 99° C.

<OCP Shaped Product>

The OCP shaped product in the present invention preferably contains 10% by mass or more of OCP in composition, more preferably contains 50% by mass or more of OCP in composition, further preferably contains 70% by mass or more of OCP in composition, and particularly preferably contains 90% by mass or more of OCP in composition. Particularly, when it is used as a bone regeneration material, in addition to the conditions described above, the proportion of HAp in the shaped product is preferably 10% by mass or less, more preferably 5% by mass or less, further preferably 1% by mass or less, and particularly preferably unable to be detected.

The shaped product herein is cured and keeps its morphology without any intervening substance such as collagen in between through a chemical bond of crystals of an inorganic substance including OCP, which is a constituent of an inorganic component, or entanglement or fusion between crystals. It also keeps its morphology without being collapsed even when it is immersed in at least 99.5% ethanol or water for 24 hours. Accordingly, an OCP powder compact, which is shaped by compressing OCP powder, is not encompassed in this term.

The chemical bond herein refers to that one or more chemical bonds categorized as any of covalent bond, ionic bond, hydrogen bond and metallic bond are present between crystals constituting the inorganic component, and crystals are fixed to each other due to these bonds, thereby stabilizing the positional relationship between crystals and maintaining a general form of the shaped product.

The entanglement between crystals herein refers to that a plurality of crystals microscopically constituting the shaped product take a structure in which they are in contact with each other via their crystal planes, and a plurality of crystals are fixed by this mechanism, thereby maintaining a general form of the shaped product.

The fusion between crystals herein refers to that a plurality of crystals constituting the shaped product are in contact with each other via their crystal planes with no void in some moieties, and no grain boundary can be observed in these moieties.

The shape of the shaped product produced in the present invention takes over the shape of the precursor ceramic composition. As such, by using a precursor ceramic composition to which precise processing can be carried out, complicated shapes such as a communicating porous structure and honeycomb structure can be imparted to the shaped product.

The shape of the OCP shaped product in the present invention is not particularly limited. As described above, the OCP shaped product practically takes over the shape of the precursor ceramic composition, and therefore, its shape is practically determined by the shape of the precursor ceramic composition. Specifically, examples of the shape of the OCP shaped product include, for example, disc, block and sheet.

The size of the disc is not particularly limited, but its diameter is, for example, 1 to 20 mm, and is preferably 5 to 10 mm. The thickness is, for example, 0.5 to 5 mm, and is preferably 1 to 3 mm.

The size of the block is not particularly limited, but for example, the block has a length of 1 to 15 mm, a width of 1 to 50 mm and a height of 0.5 to 100 mm, and preferably has a length of 8 to 12 mm, a width of 10 to 30 mm and a height of 10 to 50 mm.

The size of the sheet is not particularly limited, but for example, the sheet has a length of 1 to 20 mm, a width of 1 to 20 mm and a thickness of 0.01 to 0.5 mm, and preferably has a length of 5 to 15 mm, a width of 5 to 15 mm and a thickness of 0.05 to 0.3 mm.

The pore size and internal structure of the OCP shaped product in the present invention are not particularly limited. For example, the pore size is normally 0 to 2000 µm, and is preferably 50 to 300 µm. The internal structure may be a single pore structure, or a communicating porous structure having an arbitrary shape. The aspect ratio is not particularly limited. The porosity (void ratio) is 0 to 99%, and is preferably 40 to 80%.

A method of producing the porous structure is not particularly limited. The porous structure may be formed by allowing granules of the precursor ceramic composition to bond to each other through crystal growth, by adding a readily soluble salt as a void forming agent, by producing a porous structure by extrusion molding, or by adding a pore forming agent composed of organic substances, which is burned out when sintered.

On the OCP shaped product in the present invention, a molecule having a functional group that chemically bonds to calcium, such as a carboxyl group, a silanol group, a phosphoric acid group, a sulfo group, a hydroxyl group and a thiol group, in composition can be supported. When it is desired to have a molecule having a functional group that chemically bonds to calcium supported on the OCP shaped product, the molecule having a functional group that chemically bonds to calcium in composition may be allowed to be contained in the immersion solution or in the precursor ceramic composition in advance. It is noted that an OCP including a functional group that chemically bonds to calcium in composition is herein defined as an inorganic substance.

The molecule having a carboxyl group herein refers to a molecule having one or more functional groups represented by —COOH in composition.

For the molecule having a carboxyl group to be supported on the OCP shaped product, a substance categorized as a monocarboxylic acid, a dicarboxylic acid, a tricarboxylic acid, a thiol carboxylate, a halogenated carboxylic acid, an amino acid, an aromatic acid, a hydroxy acid, a saccharic acid, a nitrocarboxylic acid, polycarboxylic acid and the like, a derivative thereof, and a substance obtained by polymerizing them are used. In other words, examples thereof include acetic acid, propionic acid, butyric acid, formic acid, valeric acid, succinic acid, citric acid, mercaptoundecanoic acid, thioglycolic acid, asparagusic acid, α-lipoic acid, β-lipoic acid, dihydrolipoic acid, chloroacetic acid, malonic acid, aconitic acid, malic acid, oxalic acid, tartaric acid, malonic acid, glutaric acid, adipic acid, fumaric acid, maleic acid, oxalacetic acid, α-ketoglutaric acid, oxalosuccinic acid, pyruvic acid, isocitric acid, α-alanine, β-alanine, arginine, asparagine, aspartic acid, cysteine, glutamine, glutamic acid, glycine, histidine, isoleucine, leucine, lysine, methionine, phenylalanine, proline, serine, threonine, tryptophan, thyrosin, valine, cysteine, hydroxyproline, o-phosphoserine, desmosine, nopaline, octopine, mannopine, saccharopine, N-methylglycine, dimethylglycine, trimethylglycine, citrulline, glutathione, creatine, γ-aminobutyric acid, theanine, lactic acid, folinic acid, folic acid, pantothenic acid, benzoic acid, salicylic acid, o-phthalic acid, m-phthalic acid, p-phthalic acid, nicotinic acid, picolinic acid, gallic acid, mellitic acid, cinnamic acid, jasmonic acid, undecylenic acid, levulinic acid, iduronic acid, glucuronic acid, galacturonic acid, glyceric acid, gluconic acid, muramic acid, sialic acid, mannuronic acid, glycolic acid, glyoxylic acid, ethylenediamine tetraacetic acid (EDTA), nitroacetic acid, nitrohydrocinnamic acid, nitrobenzoic acid, polyacrylic acid, polycitric acid, polyitaconic acid, and salts thereof. One of these molecules may be supported singly, or they may be used in combination.

The molecule having a silanol group herein refers to a molecule having a functional group represented by $\gamma$-$SiO_4R_3$ in composition, wherein R is H or an alkyl group.

Examples of the molecule having a silanol group to be supported on the OCP shaped product include γ-methacryloxypropyltrimethoxysilane (γ-MPTS), tetraethyl orthosilicate (TEOS), sodium silicate, orthosilicic acid, metasilicic acid, metabisilicic acid, and salts thereof. One of these molecules may be supported singly, or they may be used in combination.

The molecule having a phosphoric acid group herein refers to a molecule having a functional group represented by —$PO_4R_2$ in composition, wherein R is H or an alkyl group.

Examples of the molecule having a phosphoric acid group to be supported on the OCP shaped product include adenosine triphosphate (ATP), adenosine diphosphate (ADP), nucleotides, glucose-6-phosphate, flavin mononucleotide, polyphosphoric acid, 10-methacryloyloxydecyl dihydrogen phosphate (MDP), phytic acid, and salts thereof. These molecules may be supported singly, or they may be used in combination.

The molecule having a sulfo group herein refers to a molecule having a functional group represented by —$SO_3R$ in composition, wherein R is H or an alkyl group.

Examples of the molecule having a sulfo group to be supported on the OCP shaped product include benzenesulfonic acid, taurine, sodium linear alkylbenzene sulfonate, xylene silanol, bromophenol blue, methyl orange, 4,4'-diisothiocyano-2,2'-stilbenedisulfonic acid (DIDS), azorubine, amaranth, indigo carmine, water blue, cresol red, coomassie brilliant blue, congo red, sulfanilic acid, tartrazine, thymol blue, tosyl azide, new coccine, pyranine, methylene blue, hydroxyethyl piperazine ethanesulfonic acid (HEPES), sodium cyclamate, saccharin, taurocholic acid, isethionic acid, cysteic acid, 10-camphorsulfonic acid, 4-hydroxy-5-aminonaphthalene-2,7-disulfonic acid, methanesulfonic acid, ethanesulfonic acid, and salts thereof. One of these molecules may be supported singly, or they may be used in combination.

The molecule having a hydroxyl group herein refers to a molecule having a functional group represented by —OH in composition.

Examples of the molecule having a hydroxyl group to be supported on the OCP shaped product include a compound categorized as an alcohol, 2-hydroxyethyl methacrylate (HEMA), hydroxylamine, hydroxamic acid, phenol, a compound categorized as an aldol, a compound categorized as a saccharide, a compound categorized as a glycol, inositol, a compound categorized as a sugar alcohol, pantetheine, and salts thereof. One of these molecules may be supported singly, or they may be used in combination.

The molecule having a thiol group herein refers to a molecule having a functional group represented by —SH in composition, wherein R is H or an alkyl group.

Examples of the molecule having a thiol group to be supported on the OCP shaped product include captopril, methanethiol, ethanethiol, cysteine, glutathione, thiophenol, acetylcysteine, 1,2-ethanedithiol, cysteamine, dithioerythritol, dithiothreitol, dimercaprol, thioglycolic acid, thiopronine, 2-naphthalenethiol, bucillamine, furan-2-ylmethanethiol, D-penicillamine, mycothiol, mesna, 3-methyl-2-butene-1-thiol, 3-mercaptopyruvic acid, and salts thereof. These molecules may be supported singly, or they may be used in combination.

The salts thereof mean salts of compounds, especially salts that dissolve satisfactorily when it is brought into contact with a solvent such as distilled water and function in the same manner as the compounds described above. Those salts encompass not only anhydrous salts of the compounds described above, but also hydrate salts thereof, of course. Examples of those salts include, for example, alkali metal salts such as sodium salt, potassium salt, lithium salt, rubidium salt and cesium salt; alkaline earth metal salts excluding Ca salt such as magnesium salt and strontium salt; aluminum salt; zinc salt; transition metal salts such as iron salt, nickel salt, cobalt salt and copper salt; inorganic salts such as ammonium salt; organic amine salts such as tris (hydroxymethyl)aminomethane salt, phenylglycine alkyl ester salt, dicyclohexylamine salt, N,N'-dibenzylethylenediamine salt, ethylenediamine salt, glucosamine salt, guanidine salt, diethylamine salt, triethylamine salt, N-methylglucamine salt, t-octylamine salt, dibenzylamine salt, morpholine salt, procaine salt, diethanolamine salt, N-benzyl-N-phenethylamine salt, piperazine salt, chloroprocaine salt and tetramethylammonium salt; and phenol salt.

The concentration of the substance including a functional group that chemically bonds to calcium in composition contained in the immersion solution is not particularly limited. It is normally 0 to 2 mol/L, and is preferably 0.01 to 0.5 mol/L.

When it is desired to have another substance (compound) supported in addition to the substance including a functional group that chemically bonds to calcium in composition, it is necessary to add the compound to at least one of the precursor ceramic composition and the immersion solution in advance. It is noted that an OCP on which the other compound is supported in addition to the substance including a functional group that chemically bonds to calcium in composition is herein also defined as an inorganic substance.

Examples of the type of compounds to be supported include known antimicrobial agents, antibiotics, anticancer agents, antiseptic agents and acid tolerance improving agents.

Examples of the compound to be supported include elements such as silver, selenium, platinum, gold, palladium, iridium, osmium, rhenium, gallium, germanium, tellurium, titanium and bismuth, and ions, complexes, clusters and nanoparticles thereof; penicillin antibiotics such as penicillin G procaine (penicillin G-procaine salt), benzylpenicillin benzathine (benzylpenicillin-benzathine salt), fusidic acid, fusafungin, phosphomycin, mupirocin, rodemprim, dirithromycin, benzyl penicillin, phenoxymethyl penicillin, methicillin, ampicillin, cloxacillin, carbenicillin, pivampicillin, amoxicillin, talampicillin, bacampicillin, ticarcillin, azlocillin, mezlocillin, pivmecillinam, piperacillin, amoxicillin-clavulanic acid, apalcillin, temocillin, ticarcillin-clavulanic acid, ampicillin-sulbactam, sultamicillin and piperacillin-tazobacatm; streptomycin antibiotics such as streptomycin; chloramphenicol antimicrobial agents such as chloramphenicol and thiamphenicol; glycopeptide antibiotics such as vancomycin and teicoplanin; tetracycline antibiotics such as chlorotetracycline, aureomycin, chloramphenicol oxytetracycline, demethylchlortetracycline, ledermycin, lymecycline, doxycycline, demeclocycline and minocycline; aminoglycoside antibiotics such as gentamycin, neomycin, spectinomycin, tobramycin, amikacin, micronomicin, isepacin and arbekacin; cephalosporin antibiotics such as cefuroxime, cefaclor, cefotaxime, cefsulodin, cefoperazone, cefazolin, cefradine, cefadroxil, cefamandole, cefotiam, cefalexin, cefonicid, cefpiramide, cefoperazone-sulbactam, cefodizime, ceftibufen, cefpodoxime, cefdinir, cefetamet, cefpirome, cefprozil, ceftriaxone, cefmenoxime, ceftazidime, ceftiroxime and cefepime; polypeptide antibiotics such as colistin; macrolide antibiotics such as roxithromycin, azithromycin, midecamycin, erythromycin, spiramycin and clarithromycin; streptogramin antibiotics such as virginiamycin and pristinamycin; carbacephem antibiotics such as loracarbef; sulfa agents such as sulphamethizole, sulfacetamide, sulfamerazine, sulphadimidine and sulfadiazine; quinolone antimicrobial agents such as levofloxacin, fleroxacin, nadifloxacin, norfloxacin, ofloxacin, ciprofloxacin, enrofloxacin, lomefloxacin, rufloxacin and sparfloxacin; ketolide antibiotics such as erythromycin; carbapenem antibiotics such as panipenem-betamipron; lincomycin antibiotics such as clindamycin; oxacephem antibiotics such as latamoxef and flomoxef; carbapenem antibiotics such as imipenem-cilastatin; cephamycin antibiotics such as cefoxitin, cefmetazole and cefotetan; monobactam antibiotics such as aztreonam; and nonsteroidal antiinflammatory drugs such as acetaminophen, acetylsalicylic acid, ethenzamide, salicylamide, diclofenac, phenylacetic acid, indomethacin, loxoprofen, ibuprofen, ketoprofen, naproxen, piroxicam, misoprostol, meloxicam and lornoxicam.

Examples of the anticancer agent to be supported include platinum complexes such as cyclotriphosphazene-platinum complex composite, cisplatin, nedaplatin, oxaliplatin and carboplatin; antimetabolites such as 5-fluorouracil (5-FU), tegafur, tegafur-uracil and methotrexate; anticancer streptococcal formulations such as OK-432; anticancer polysaccharides such as krestin, lentinan, schizophyllan and sonifilan; anticancer antibiotics such as doxorubicin hydrochloride, mitomycin C, actinomycin D, bleomycin hydrochloride, bleomycin sulfate, daunorubicin hydrochloride, neocarzinostatin, aclarubicin hydrochloride and epirubicin hydrochloride; enzymes such as asparaginase; mitotic inhibitors such as vinblastine; topoisomerase inhibitors such as etoposide; biological response modifiers such as interferon; antimetabolites such as cytosine arabinoside, oxyurea and N-{5-[N-(3,4-dihydro-2-methyl-4-oxoquinazolin-6-yl-methyl)-N-methylamino]-2-thenoyl}-L-glutamic acid; intercalating antibiotics such as adriamycin and bleomycin; antiestrogens such as tamoxifen; plant alkaloids such as vincristine; and anticancer antibiotics such as mitomycin C, actinomycin D, bleomycin hydrochloride, bleomycin sulfate, daunorubicin hydrochloride, doxorubicin hydrochloride, neocarzinostatin, aclarubicin hydrochloride, aclacinon and epirubicin hydrochloride.

Other than the antimicrobial agents, antibiotics, anticancer agents and acid tolerance agents described above, compounds that do not fall within the scope thereof may be supported depending on use. In other words, examples thereof include flavin mononucleotide, riboflavin, adenine, guanine, thymine, cytosine, uracil, caffeine, nicotine, atropine, nitrogen mustard, pralidoxime methiodide, deoxyribose, ascorbic acid, thiamine, galactosamine, N-acetylgalactosamine, idose, α-acetolactone, γ-butyrolactone, glycerin, ethylene glycol, iodoform, chloroform, bromoform and folinic acid.

The number of atoms in the compound to be supported is not particularly limited. It is preferably 200 or less.

One embodiment preferred as a bone regeneration material is a composite consisting only of OCP and a material already known as a bone substituting regeneration material, and does substantially not contain other components.

Examples for a material known as the bone substituting regeneration material include β-TCP, α-TCP, CSD, CSH, CSA, DCPD, calcium carbonate, $CO_3Ap$ and ACP.

The ratio of the material known as the bone substituting regeneration material and OCP is not particularly limited as long as the shaped product is constituted such that OCP is contained therein in a proportion of 10% by mass or more relative to the entire shaped product. Taking the embedding site and general condition into consideration, the composition and ratio can be changed depending on use.

Further, it is preferable that 97.5% by mass or more of the OCP shaped product in the present invention is composed of inorganic components, and it is more preferable that 99.0% by mass or more of the shaped product is composed of inorganic components.

Hereinafter, specific examples will be described for embodiments of the present invention, but the present invention is not limited thereto.

EXAMPLES

Example 1

(Producing of OCP Shaped Product from Composition Comprising Calcined Gypsum as Main Component)
(1) Producing of Precursor Ceramic Composition Under room temperature conditions, 3 g of CSH ($CaSO_4 \cdot 1/2H_2O$) and 2 g of NaDP ($NaH_2PO_4 \cdot 2H_2O$), both purchased from Wako Pure Chemical Industries, Ltd., were kneaded with 0.8 mL of distilled water for 2 minutes, using a spatula at a kneading rate of 120 rpm in a mortar. The kneaded product was embedded in a split mold with φ6 mm×3 mm and shaped. After the shaping, the resultant was left to rest under room temperature for 12 hours, and was sufficiently cured and dried, providing a CSH-NaDP composition, which is one precursor ceramic composition.

This CSH-NaDP composition is a mixture of ceramics having a solubility in $H_2O$ higher than that of OCP, and when it is immersed in distilled water, the surrounding solution has a pH of 4.5. The solubility in distilled water ($H_2O$) of CSH is 2.60 g/L, and the solubility in distilled water ($H_2O$) of NaDP is 949.0 g/L.

FIG. 1-1 (A) shows a photograph of the CSH-NaDP composition, which is the produced precursor ceramic composition, and FIG. 1-1 (B) shows the XRD pattern thereof.
(2) Producing of OCP Shaped Product Through Composition Conversion Reaction The CSH-NaDP composition produced in (1) described above was immersed in 15 mL of a 1 mol/L aqueous solution of disodium hydrogen phosphate at 37° C., 60° C. or 80° C., and was allowed to react for 12 hours to 10 days. Specifically, the reaction was performed at 37° C. for 12 hours, 1 day or 10 days, at 60° C. for 12 hours, 1 day or 10 days, or at 80° C. for 12 hours, 1 day or 10 days. The shaped product after the reaction was washed with distilled water three times or more, and was left to rest and dried in a thermostatic chamber at 37° C. for 6 hours. The 1 mol/L aqueous solution of disodium hydrogen phosphate before the reaction had a pH of 9.5 at room temperature. The aqueous solution after the reaction at 80° C. for 1 day had a pH of 6.8 at room temperature. In this system, the stable phase is an apatite.

The 1 mol/L aqueous solution of disodium hydrogen phosphate herein refers to a solution formed by completely dissolving 141.96 g of disodium hydrogen phosphate anhydrous or 156.01 g of disodium hydrogen phosphate dihydrate in distilled water such that the total amount of the formed solution is 1 L. The amount of disodium hydrogen phosphate, disodium hydrogen phosphate and distilled water can be changed as long as the ratio of disodium hydrogen phosphate or disodium hydrogen phosphate dihydrate and distilled water is the same as above.
(3) Characterization of OCP Shaped Product The OCP shaped product produced in the present Example was characterized by a powder X-ray diffraction (XRD) and Fourier transform infrared spectroscopy (FT-IR). Using an X-ray diffraction apparatus (D08 ADVANCE, Bruker AXS GmbH) with a radiation source of CuKα radiation, 40 kV, 40 mA, the XRD pattern was recorded by step scanning with an interval of 0.02° from 3.0° to 70.0°. The crystalline phase was identified using the JCPDS card number: 26-1056 for OCP and the JCPDS number: 9-432 for HAp.
(4) Measurement of Mechanical Properties of OCP Shaped Product The shape and microstructure of the OCP shaped product produced in the present Example were investigated using a scanning electron microscope (SEM) S-3400N produced by Hitachi High-Technologies Corporation operating at an acceleration voltage of 5 kV. After photographing the internal structure using a micro CT photographing system, Skyscan 1076 produced by TOYO Corporation operating at an acceleration voltage of 67 kV and 160 µA, the void ratio of the OCP shaped product was analyzed and calculated using a public free software, ImageJ. For the diametral tensile strength (DTS) of the OCP shaped product, the measurement was carried out using a universal testing machine, AGS-J produced by Shimadzu Corporation with a head moving speed of 0.5 mm/min.
(5) Temperature Dependence of Formation of OCP Shaped Product FIG. 1-2 shows photographs of shaped products obtained by immersing the CSH-NaDP composition in the 1 mol/L aqueous solution of disodium hydrogen phosphate at different temperatures. The size of each shaped product is φ6 mm×3 mm. FIG. 1-3 shows XRD patterns of shaped products obtained through the immersion in the 1 mol/L aqueous solution of disodium hydrogen phosphate.

As shown in FIG. 1-2 and FIG. 1-3, the CSH-NaDP composition immersed in the 1 mol/L aqueous solution of disodium hydrogen phosphate at 37° C. became a shaped product comprising OCP as main component after the immersion for 10 days. The CSH-NaDP composition immersed in the 1 mol/L aqueous solution of disodium hydrogen phosphate at 60° C. became a shaped product comprising OCP as main component after the immersion for 1 day. The CSH-NaDP composition immersed in the 1 mol/L aqueous solution of disodium hydrogen phosphate at 80° C. became a shaped product consisting of a single phase of OCP after the immersion for 1 day.

(6) Mechanical Properties of OCP Shaped Product

As shown in FIG. 1-4, the shaped product produced by immersing the CSH-NaDP composition in the 1 mol/L aqueous solution of disodium hydrogen phosphate at 80° C. for 1 day had a DTS strength of 0.95±0.16 MPa.

(7) Microstructure of OCP Shaped Product

As shown in SEM photographs of FIG. 1-5, it was observed that the shaped product produced by immersing the CSH-NaDP composition in the 1 mol/L aqueous solution of disodium hydrogen phosphate at 80° C. for 1 day has a structure in which plate crystals with a length of 2 to 5 μm, a width of 0.2 to 1 μm, and a thickness of 0.01 to 0.2 μm are precisely entangled. This structure is believed to be made of OCP crystals because it was not observed in the CSH-NaDP composition before the immersion.

Example 2

(Producing of OCP Shaped Product with Communicating Porous Structure from Composition Comprising Calcined Gypsum as Main Component Having Communicating Porous Structure)

(1) Producing of Precursor Ceramic Composition with Communicating Porous Structure from Precursor Ceramic Granules A CSH-NaDP precise shaped product (CSH-NaDP composition) produced by the same technique as Example 1 was pulverized with a mortar and pestle, and granulated. These granules were classified using a sieve such that the particle size is 200 to 300 μm. The classified granules were packed in a split mold with φ6 mm×3 mm. To this, 0.2 mL of 70% ethanol saturated with CSH and NaDP was added dropwise, partially dissolving the surface of granules. Then, the resultant was left to rest and dried at room temperature for 12 hours or more. As a result, the granules were allowed to bond to each other, and a CSH-NaDP composition with a communicating porous structure was produced.

FIG. 2-1 (A) shows a photograph of the CSH-NaDP composition with a communicating porous structure, which is the produced precursor ceramic composition, and FIG. 2-1 (B) shows a micro CT image thereof.

(2) Producing of OCP Shaped Product with Communicating Porous Structure Through Composition Conversion Reaction The CSH-NaDP composition with a communicating porous structure produced in (1) described above was immersed in 15 mL of a 1 mol/L aqueous solution of disodium hydrogen phosphate at 80° C., and was allowed to react for 1 day (24 hours).

(3) Characterization of OCP Shaped Product with Communicating Porous Structure

Characterization was carried out by the same method as Example 1(3).

(4) Measurement of Mechanical Properties of OCP Shaped Product with Communicating Porous Structure Measurement was carried out by the same method as Example 1(4).

(5) Properties of OCP Shaped Product with Communicating Porous Structure

FIG. 2-2 (A) shows a photograph of the shaped product produced through the immersion in the 1 mol/L aqueous solution of disodium hydrogen phosphate at 80° C. for 1 day (24 hours), and FIG. 2-2 (B) shows a micro CT image thereof. Further, FIG. 2-3 shows the XRD pattern thereof. Furthermore, FIGS. 2-4 (A) and (B) show SEM photographs of the CSH-NaDP composition with a communicating porous structure after the immersion (OCP shaped product with a communicating porous structure), and FIGS. 2-4 (C) and (D) show SEM photographs of the CSH-NaDP composition with a communicating porous structure before the immersion.

As shown in FIG. 2-2, it was observed that a general form and the porous structure are maintained even after the immersion. As shown in FIG. 2-3, from the XRD pattern of the sample, it was found that the composition with a communicating porous structure after the immersion was composed of a single phase of OCP. As shown in FIG. 2-4, SEM observation of the sample revealed that, while the shape in which granules are linked to each other is maintained, plate crystals are formed in a granular form.

[Confirmation of Utility of Shaped Product of the Present Invention Through Animal Test]

Prior to the experiment, approval by the Animal Care and Use Committee of Kyushu University was obtained, and the experiment was then carried out (approval number: A28-270-0). Male, Japanese white rabbits (Japan SLC, Inc.) with a body weight of 3.0 to 3.5 kg were used. Ketamine (30 mg/kg) and xylazine (50 mg/kg) were intramuscularly injected to the buttocks for sedation, the ear vein was secured and then maintained by intravenous anesthesia of ketamine (10 mg/kg) and xylazine (3 mg/kg). After disinfecting the knee region with an antiseptic solution, the skin and the periosteum were incised to develop the distal part of femur head. The periosteum was peeled apart with a raspatory, and then, a bone defect with a size of φ6.25 mm×3 mm was formed using a trephine bar on the inner side of femur. Into this, the OCP shaped product produced from the CSH-NaDP composition (Example 1) and the OCP shaped product with a communicating porous structure produced from the CSH-NaDP composition with a communicating porous structure (Example 2) were embedded. Further, a hydroxyapatite sintered body was similarly embedded as a control. The outer diameters of the embedded samples are all φ6 mm×3 mm. After the embedding, the periosteum and skin were sutured, and 2% lidocaine was injected to a peripheral part of the surgical field.

2 weeks or 4 weeks after the embedding, the animals were sacrificed by excessive anesthesia. After confirming cardiac arrest and loss of pupillary reaction, the embedded object was excised along with surrounding tissues, and fixed with 4% paraformaldehyde. After the fixation, the sample was subjected to decalcification treatment approximately for 2 weeks in a 10% aqueous solution of EDTA or an aqueous solution for rapid decalcification (KC-X). The sample was then washed with water, gradually dehydrated with a series of ethanols, and embedded in paraffin. The center of the bone defect part in femur head was taken out, and by sagittally sectioning the sample with a microtome, a slice of about 5 μm was made. The slice thus made was stained with hematoxylin-eosin (HE), and photographed under ordinary light with a photomicrographic camera produced by KEYENCE CORPORATION (BZ-X710).

The histopathological image stained with HE was investigated.

FIG. 2-5 shows HE stained tissue images taken 2 weeks after the embedding in the rabbit femur head, and (A) is of the OCP shaped product produced in Example 1, (B) is of the OCP shaped product with a communicating porous structure produced in Example 2, and (C) shows the hydroxyapatite sintered body, which is a control.

As shown in FIGS. 2-5 (A) and (B), new bone formation was observed around the OCP shaped product and the OCP shaped product with a communicating porous structure, which had been embedded in the bone defect part in rabbit femur head. With the OCP shaped product with a communicating porous structure, a state in which a new bone is penetrated into a part of the inside of the porous structure was also observed. Furthermore, in both of the OCP shaped product and the OCP shaped product with a communicating porous structure, a state in which a part of the embedded sample is substituted by bone was also observed. With the OCP shaped product, a part of the periphery of the shaped product was substituted by a bone, but with the OCP shaped product with a communicating porous structure, a state in which a bone is penetrated into the inside and substitutes a part of the OCP shaped product with a communicating porous structure was observed.

FIG. 2-6 shows HE stained tissue images taken 4 weeks after the embedding in the rabbit femur head, and (A) is of the OCP shaped product produced in Example 1, (B) is of the OCP shaped product with a communicating porous structure produced in Example 2, and (C) is of the hydroxyapatite sintered body, which is a control.

As shown in FIG. 2-6, in the tissue slice 4 weeks after the embedding, compared to that 2 weeks after the embedding, a state in which the OCP shaped product and the OCP shaped product with a communicating porous structure are substituted by bone was observed. With the OCP shaped product, approximately 30% of the shaped product was substituted by a new bone from the outside. With the OCP shaped product with a communicating porous structure, in addition to the effect described above, a state in which a bone penetrates into the central part of the OCP shaped product with a communicating porous structure, thereby causing active bone substitution even inside was observed.

Example 3

(Producing of OCP Shaped Product from DCPD Composition)
(1) Producing of Precursor DCPD Composition In a split mold with φ6 mm×3 mm, 0.1 g of α-TCP ($Ca_3PO_4$, α-TCP-B) purchased from Taihei Chemical Industrial Co., Ltd. was embedded. To this, 200 μL of a 2 mol/L aqueous phosphoric acid solution ($H_3PO_4$) was added dropwise, and the resultant mixture was left to rest for 3 minutes and cured, providing a α-TCP/$H_3PO_4$ composition (precursor DCPD composition), which is one precursor ceramic composition. FIG. 3-1 (A) shows a photograph of the DCPD composition, which is the produced precursor ceramic composition, and FIG. 3-1 (B) shows the XRD pattern thereof. In the composition after the curing, a peak corresponding to DCPD appears, and this was defined as the DCPD composition, which is the precursor ceramic composition.

This DCPD composition has a solubility in $H_2O$ higher than that of OCP, and when it is immersed in distilled water, the surrounding solution has a pH of 6.7. The solubility in $H_2O$ of DCPD is 0.32 g/L.

(2) Producing of OCP Shaped Product Through Composition Conversion Reaction

In a thermostatic chamber at 4° C., room temperature, 37° C., 70° C. or 80° C., the precursor DCPD composition produced in (1) described above was immersed in 15 mL of a 1 mol/L aqueous solution of disodium hydrogen phosphate, and was allowed to react for 1 day to produce an OCP shaped product. The 1 mol/L aqueous solution of disodium hydrogen phosphate before the reaction had a pH of 9.5. Each solution after the reaction had a pH of 9.0, 8.7, 8.3, 7.7 or 7.4. In this system, the stable phase is an apatite.

(3) Characterization of OCP Shaped Product

Characterization of the OCP shaped product and measurement of mechanical properties thereof were carried out in the same manner as (3) and (4) of Example 1.

(4) Temperature Dependence of Producing of OCP Shaped Product

FIG. 3-2 shows photographs of the DCPD shaped products (OCP shaped products) after the immersion.

FIG. 3-3 shows XRD patterns of the DCPD shaped products (OCP shaped products) after the immersion in the 1 mol/L aqueous solution of disodium hydrogen phosphate at 4° C. to 80° C. for 1 day.

As shown in FIG. 3-2, when the shaped products were immersed in the 1 mol/L aqueous solution of disodium hydrogen phosphate for 1 day, they did not exhibit a collapsed state under any temperature condition.

Further, as shown in FIG. 3-3, the shaped products immersed under any temperature condition exhibit a characteristic peak in the vicinity of 4.7° in their XRD patterns, and a state in which OCP is formed was observed. In case of 4° C., room temperature and 37° C., DCPD was still present in any of the shaped products, and therefore, the shaped products are composed of two phases, DCPD and OCP. In case of 70° C., only OCP is detected in the shaped product, and therefore, it is an OCP shaped product. In case of 80° C., the shaped product contains HAp in addition to OCP.

(5) Relationship of Immersion Time and Producing of OCP Shaped Product from Precursor Ceramic Composition Characterization was carried out by XRD with varying immersion times, 2 days, 3 days and 7 days, under the same temperature and solution conditions. The results are shown in FIG. 3-4 to FIG. 3-7.

First, as shown in FIG. 3-2, a general form of the precursor DCPD shaped product was maintained under all temperature and time conditions. As shown in FIG. 3-4, in case of 4° C. and room temperature, a state in which DCPD in the precursor ceramic composition is still present even after the immersion for 7 days was observed. As shown in FIG. 3-5, in case of 37° C., DCPD was still present after 3 days, but it was present only in a trace amount after the immersion for 7 days. As shown in FIG. 3-6, in case of 70° C., a shaped product consisting of a single phase of OCP was obtained after the immersion for 2 days and 3 days. Further, an OCP shaped product containing a trace amount of HAp was obtained after the immersion for 7 days. On the other hand, as shown in FIG. 3-7, it was found that, in case of 80° C., a shaped product is composed of two phases, HAp and OCP, practically consisting of HAp after the immersion for 2 days, and therefore, further investigation was not carried out.

(6) Relationship between Immersion Time and Mechanical Strength

As an index for the mechanical strength of OCP shaped products, the diametral tensile strength (DTS) was measured by the same method as Example 1(4). Investigation was carried out for systems immersed in the 1 mol/L aqueous solution of disodium hydrogen phosphate at an immersion temperature of 70° C. and for an immersion time of 1 day, 2 days, 3 days and 7 days, which are conditions by which shaped products consisting of a single phase of OCP were obtained in the investigation for temperature dependence in (5) described above.

As shown in FIG. 3-8, the shaped product immersed in the 1 mol/L aqueous solution of disodium hydrogen phosphate for 1 day had a DTS strength of about 2.12±0.23 MPa. The shaped product immersed for 2 days had a DTS strength of about 5.88±1.71 MPa, which is significantly increased as compared to the DTS strength of the shaped product immersed for 1 day. The shaped product immersed for 3 days had a DTS strength of about 3.55±1.05 MPa and the shaped product immersed for 7 days had a DTS strength of about 3.71±1.47 MPa, which are significantly decreased as compared to the DTS strength of the shaped product immersed for 2 days.

Example 4

(Producing of OCP Shaped Product Supporting Molecule Containing Carboxyl Group in Composition f)
(1) Producing of OCP Shaped Product Supporting Molecule Containing Carboxyl Group in Composition A precursor DCPD composition produced by the same technique as Example 3(1) was immersed in a 1 mol/L aqueous solution of disodium hydrogen phosphate containing 0.2 mol/L of citric acid, succinic acid or tartaric acid at 70° C. for 2 days.

FIG. 4-1 shows photographs of the DCPD compositions (OCP shaped products) after the immersion. In the figure, (A) is of the shaped product immersed in the aqueous solution of disodium hydrogen phosphate containing citric acid, (B) is of the shaped product immersed in the aqueous solution of disodium hydrogen phosphate containing succinic acid, and (C) is of the shaped product immersed in the aqueous solution of disodium hydrogen phosphate containing tartaric acid. As shown in FIG. 4-1, in any case, the general form of the shaped product was maintained even after the immersion.

(2) Characterization of Shaped Product Treated in Solution Containing Molecule Containing Carboxyl Group in Composition Characterization was carried out by XRD patterns measured and obtained by the same procedures as Example 1(3). FIG. 4-2 shows the obtained XRD patterns. As shown in FIG. 4-2, XRD patterns of the OCP shaped products produced through the treatment in the aqueous solution containing 0.2 mol/L of citric acid or succinic acid both showed that the shaped products consist of a single phase of OCP. The XRD pattern of the OCP shaped product produced by treating in the aqueous solution containing 0.2 mol/L of tartaric acid showed that the shaped product is comprising OCP as main component and also contains DCPD.

(3) Supported Amount and Supporting Form of Molecule Containing Carboxyl Group in Composition Investigation was carried out for the supported amount and supporting forms of citric acid and succinic acid. These acids achieved satisfactory results in the above-described investigation for the type of carboxylic acid that can be supported on the OCP shaped product. In order to measure the concentration of carboxylic acid, carbon-hydrogen-nitrogen analysis (CHN analysis) was carried out by heating the shaped product in Ar gas flow and using an elemental analyzer produced by Yanaco (MT-6) to determine the carbon concentration in the shaped product. From the carbon content of the obtained shaped product and the molecular weight of the carboxylic acid, supporting of which was attempted, the amount of the carboxylic acid supported on the OCP shaped product was measured. For the supporting form of the carboxylic acid, infrared spectroscopy (FT-IR) was also used in combination. The FT-IR spectra were obtained by mounting the sample on an ATR prism and using a FT-IR spectrometer (FT/IR-6300, JASCO Corporation) over the range of 4,000 to 400 $cm^{-1}$ with a resolution of 2 $cm^{-1}$. FIG. 4-3 shows the obtained FT-IR spectra.

(4) Investigation for OCP Spectrum and Supporting Form of Molecule Containing Carboxyl Group in Composition As the standard for the OCP spectrum data, description in "Spectrochim Acta 23A: 1781-1792, 1967" was used.
(5) Influence on OCP Crystal Structure Given by Molecule Containing Carboxyl Group in Composition As shown in FIG. 4-3, in the IR spectrum of the OCP shaped product produced in the aqueous solution carrying 0.2 mol/L of citric acid, observed was a state in which the shape of the band attributable to the $HPO_4$—OH layer structure in the OCP crystal structure in the vicinity of 1635 $cm^{-1}$ is remarkably changed. Further, absorption bands attributable to citric acid and succinic acid, supporting of which were attempted, were observed in the vicinity of $1300^{-1}$ to 400 $cm^{-1}$. From the above, it was shown that citric acid and succinic acid are contained in the $HPO_4$—OH layer structure.
(6) Supported Amount of Molecule Containing Carboxyl Group in Composition From the results of elemental analysis, it was found that the OCP shaped product contains about 2.6% of citric acid, and 1.1% of succinic acid.
(7) Measurement of Mechanical Properties of OCP Shaped Product Supporting Molecule Containing Carboxyl Group in Composition The DCPD shaped product was immersed in a 1 mol/L aqueous solution of disodium hydrogen phosphate containing either citric acid or succinic acid at a concentration of 0.01 mol/L, 0.05 mol/L, 0.1 mol/L, 0.15 mol/L or 0.2 mol/L at 70° C. for 2 days. Further, as a control, the DCPD shaped product was similarly immersed in a 1 mol/L aqueous solution of disodium hydrogen phosphate containing neither citric acid nor succinic acid. In order to estimate mechanical properties of the shaped product after the immersion, the DTS strength was measured by the same technique as Example 1(4).

FIG. 4-4 shows the DTS strength of the OCP shaped product containing citric acid, and FIG. 4-5 shows the DTS strength of the OCP shaped product containing succinic acid.

Example 5

(Producing of OCP Shaped Product in Solution not Containing $PO_4$)

A precursor DCPD composition produced by the same technique as Example 3(1) was immersed in 15 mL of distilled water in a sealed state at 70° C. for 1 day.

FIG. 5-1 shows a photograph of the DCPD shaped product (OCP shaped product) after the immersion, and FIG. 5-2 shows the XRD pattern thereof.

As shown in FIG. 5-1, the shaped product after the immersion maintained a general form of the precursor DCPD composition. Further, as shown in FIG. 5-2, it was a shaped product containing OCP.

Further, a precursor DCPD composition produced by the same technique as Example 3(1) was immersed in 15 mL of a 1 mol/L aqueous solution of sodium sulfate in a sealed state at 70° C. for 2 days.

FIG. 5-3 shows a photograph of the DCPD shaped product (OCP shaped product) after the immersion, and FIG. 5-4 shows the XRD pattern thereof.

As shown in FIG. 5-3, the shaped product after the immersion maintained a general form of the precursor DCPD composition. Further, as shown in FIG. 5-4, it was a shaped product containing OCP.

Example 6

(Producing of OCP Shaped Product in Nonelectrolytic Nonaqueous Solution)

A precursor DCPD composition produced by the same technique as Example 3(1) was immersed in 15 mL of toluene in a sealed state at 70° C. for 2 day.

FIG. 6-1 shows a photograph of the DCPD shaped product (OCP shaped product) after the immersion, and FIG. 6-2 shows the XRD pattern thereof.

As shown in FIG. 6-1, the shaped product after the immersion maintained a general form of the precursor DCPD composition. Further, as shown in FIG. 6-2, it was a shaped product containing OCP.

Example 7

(Producing of OCP Shaped Product in Nonelectrolytic Aqueous Solution)

A precursor DCPD composition produced by the same technique as Example 3(1) was immersed in 15 mL of poly(ethylene glycol) (PEG400, Wako Pure Chemical Industries, Ltd.) or sodium polyacrylate (Sodium Polyacrylate 2,700 to 7,500, Wako Pure Chemical Industries, Ltd.) in a sealed state at 70° C. for 2 days.

FIG. 7-1 (A) shows a photograph of the DCPD shaped product (OCP shaped product) immersed in poly(ethylene glycol) and FIG. 7-1 (B) shows a photograph of the DCPD shaped product (OCP shaped product) immersed in sodium polyacrylate. Further, FIG. 7-2 shows the XRD patterns thereof.

As shown in FIG. 7-1, the OCP shaped products after the immersion maintained a general form of the DCPD shaped products. Further, as shown in FIG. 7-2, they were shaped products containing OCP.

The invention claimed is:

1. A method for producing a shaped product comprising octacalcium phosphate and having a volume of 2.0 mm$^3$ or more, comprising immersing a precursor ceramic composition containing at least one of Ca and $PO_4$ in composition, having a solubility in $H_2O$ higher than that of octacalcium phosphate, and having a volume greater than 2.0 mm$^3$, in a solution containing a component which is not contained in the precursor ceramic composition, among the components Ca, $PO_4$ and $H_2O$, which are components of octacalcium phosphate to allow the precursor ceramic composition to react, thereby converting at least a part of the precursor ceramic composition into octacalcium phosphate.

2. The method for producing a shaped product according to claim 1, wherein the precursor ceramic composition is converted into the shaped product comprising octacalcium phosphate by keeping a general form thereof.

3. The method for producing a shaped product according to claim 1, wherein the shaped product comprising octacalcium phosphate is a shaped product containing 10% by mass or more of octacalcium phosphate.

4. The method for producing a shaped product according to claim 1, comprising removing the shaped product from the solution before a reaction completion point at which the precursor ceramic composition is compositionally converted into a substance in stabilized phase.

5. The method for producing a shaped product according to claim 4, wherein the solution at the reaction completion point has a pH of 4 or more, and the reaction is terminated at a pH condition higher than the pH at the reaction completion point.

6. The method for producing a shaped product according to claim 5, wherein a calcium phosphate component at the reaction completion point is an apatite.

7. The method for producing a shaped product according to claim 4, wherein the reaction is terminated at a point at which a $Ca/PO_4$ ratio of the shaped product is lower than a $Ca/PO_4$ ratio of the shaped product at the reaction completion point.

8. The method for producing a shaped product according to claim 4, wherein the reaction is terminated at a point at which a $Ca/PO_4$ ratio of the solution is higher than a $Ca/PO_4$ ratio of the solution at the reaction completion point.

9. The method for producing a shaped product according to claim 4, wherein a pH at the reaction completion point is less than 4, and the reaction is terminated at a pH condition lower than the pH at the reaction completion point.

10. The method for producing a shaped product according to claim 9, wherein a calcium phosphate component at the reaction completion point is dicalcium phosphate anhydrous or dicalcium phosphate dihydrate.

11. The method for producing a shaped product according to claim 4, wherein the reaction is terminated at a point at which a $Ca/Pa_4$ ratio of the shaped product is higher than a $Ca/PO_4$ ratio of the shaped product at the reaction completion point.

12. The method for producing a shaped product according to claim 4, wherein the reaction is terminated at a point at which a $Ca/PO_4$ ratio of the solution is lower than a $Ca/PO_4$ ratio of the solution at the reaction completion point.

13. The method for producing a shaped product according to claim 1, comprising allowing a substance including a functional group that chemically bonds to calcium in composition to be contained in at least one of the precursor ceramic composition and the solution, so that the substance including a functional group that chemically bonds to calcium in composition is supported on an octacalcium phosphate crystal.

14. The method for producing a shaped product according to claim 13, wherein another substance is supported on the octacalcium phosphate crystal.

15. A shaped product cured by a chemical bond of an inorganic component, or entanglement or fusion between crystals of an inorganic component, wherein the shaped product contains 10% by mass or more of octacalcium phosphate and has a volume of 2.0 mm$^3$ or more.

16. The shaped product according to claim 15, wherein 97.5% by mass or more of the shaped product is composed of inorganic components.

17. The shaped product according to claim 15, wherein the shaped product has a porous structure having an arbitrary shape with a pore size in the range of 0 to 2000 μm inside thereof, and has a porosity of 0 to 99%.

18. The shaped product according to claim 15, wherein a substance having a functional group that chemically bonds to calcium in composition is supported on an octacalcium phosphate crystal.

19. The shaped product according to claim 18, wherein another substance is supported on the octacalcium phosphate crystal.

* * * * *